United States Patent [19]
Luthra et al.

[11] Patent Number: 5,965,787
[45] Date of Patent: Oct. 12, 1999

[54] HLA-DRBI PEPTIDES WITH SPECIFIC BINDING AFFINITY FOR HLA-DQ MOLECULES: PREVENTION AND TREATMENT OF RHEUMATOID ARTHRITIS

[75] Inventors: Harvinder S. Luthra; Chella S. David; Eric Zanelli, all of Rochester, Minn.

[73] Assignee: Mayo Foundation for Medical Education and Research, Rochester, Minn.

[21] Appl. No.: 08/521,871

[22] Filed: Aug. 31, 1995

[51] Int. Cl.$^6$ .............................. C12N 15/63; C12N 5/10; C12N 15/09
[52] U.S. Cl. .......................... 800/2; 435/7.2; 435/320.1; 435/172.3; 424/9.1; 424/93.21
[58] Field of Search .................................. 800/2; 435/7.2, 435/320.1, 172.3, 6; 424/93.2, 9.1; 935/62, 53, 33, 34

[56] References Cited

PUBLICATIONS

Fugger et al., *Proc. Natl. Acad. Sci. USA* 91:6151–6155, 1994.
Salvat et al., *J. of Immunology* 153:5321–5329, 1994.
Bodmer et al., *Tissue Antigens*, 39:161–175, 1992.
Bodmer et al., *Tissue Antigens*, 44:1–18, 1994.
Chen et al., *Nature*, 376:177–180, 1995.
Gonzalez–Gay et al., *J. Exp. Med.*, 180:1559–1564, 1994.
Gonzalez–Gay et al., *Immunogenetics*, 42:35–40, 1995.
E. Harris, *Ann. Intern. Med.*, 123:232–233, 1995.
Moder et al., *Regional Immunology*, 4:305–313, 1992.
Ikada et al., *Proc. Natl. Acad. Sci. USA*, 82:3410–3414, 1985.
David et al. "Role of HLA–DQ and HLA–DR transgenes in experimental arthritis implications in RA," Experimental Biology 95, Part II, Atlanta Georgia, FASEB J. vol. 9(4), abstract 5953, Apr. 9, 1995.
Zanelli et al. "DR–beta peptide reactivity of HLA–DQB10302 transgenic mice and implication for the Shared epitope hypothesis in rheumatoid arthritis," 9th International Congress of Immunology, S.F. CA, abstract 998, Jul. 23, 1995.
Nabozny et al. "Induction of Collagen induced arthritis (CIA) in HLA–DQ8 transgenic mice: Possible implication for HLA–DQ mediated susceptibility in human rheumatoid arthritis," 9th International Congress of Immunology, S.F. CA, abstract 999, Jul. 23, 1995.
Griffiths et al. "Identification of the dominant antibody reactivities to the renatured cyanogen bromide (CB) fragments of type II collagen in HLA–DQw8 transgenic mice with collagen–induced arthritis," 9th International Congress of Immunology, S.F. CA, ab, Jul. 23, 1995.
Kappel et al. "Regulating gene expression in transgenic animals," Current Opinion in Biotechnology, vol. 3: 548–553, 1992.

*Primary Examiner*—Jasemine C. Chambers
*Assistant Examiner*—Karen M. Hauda
*Attorney, Agent, or Firm*—Fish & Richardson P.C.

[57] ABSTRACT

Disclosed are transgenic mice carrying a human HLA-DQ sgene. The transgenic mice are deficient in mouse H-2 class II molecules. Such mice provide animal model systems to identify peptides useful for preventing or treating rheumatoid arthritis. Also disclosed are methods and materials for treating rheumatoid arthritis, including administration of peptides having specific binding affinity for HLA-DQ molecules expressed in a rheumatoid arthritis patient.

8 Claims, 13 Drawing Sheets

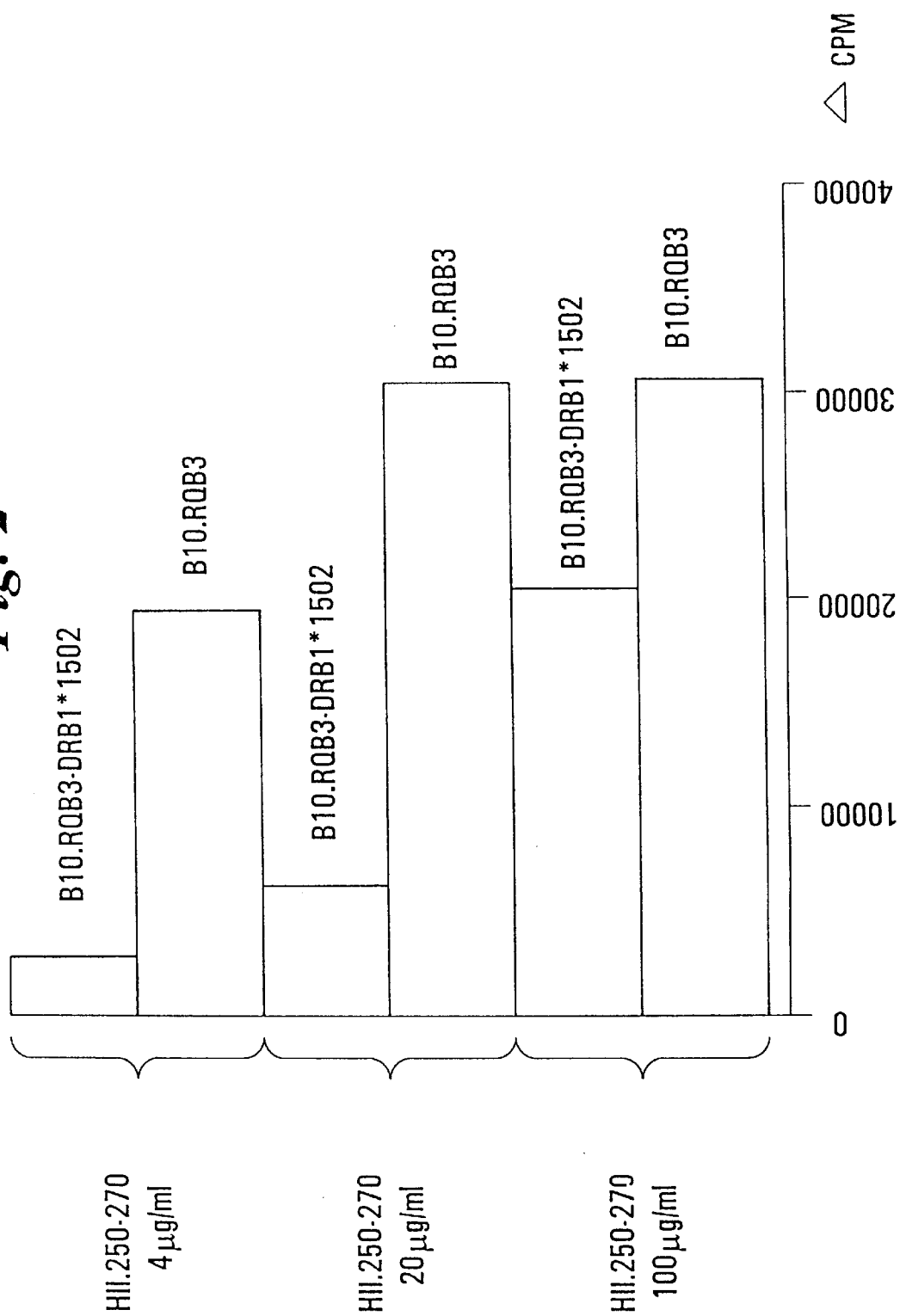

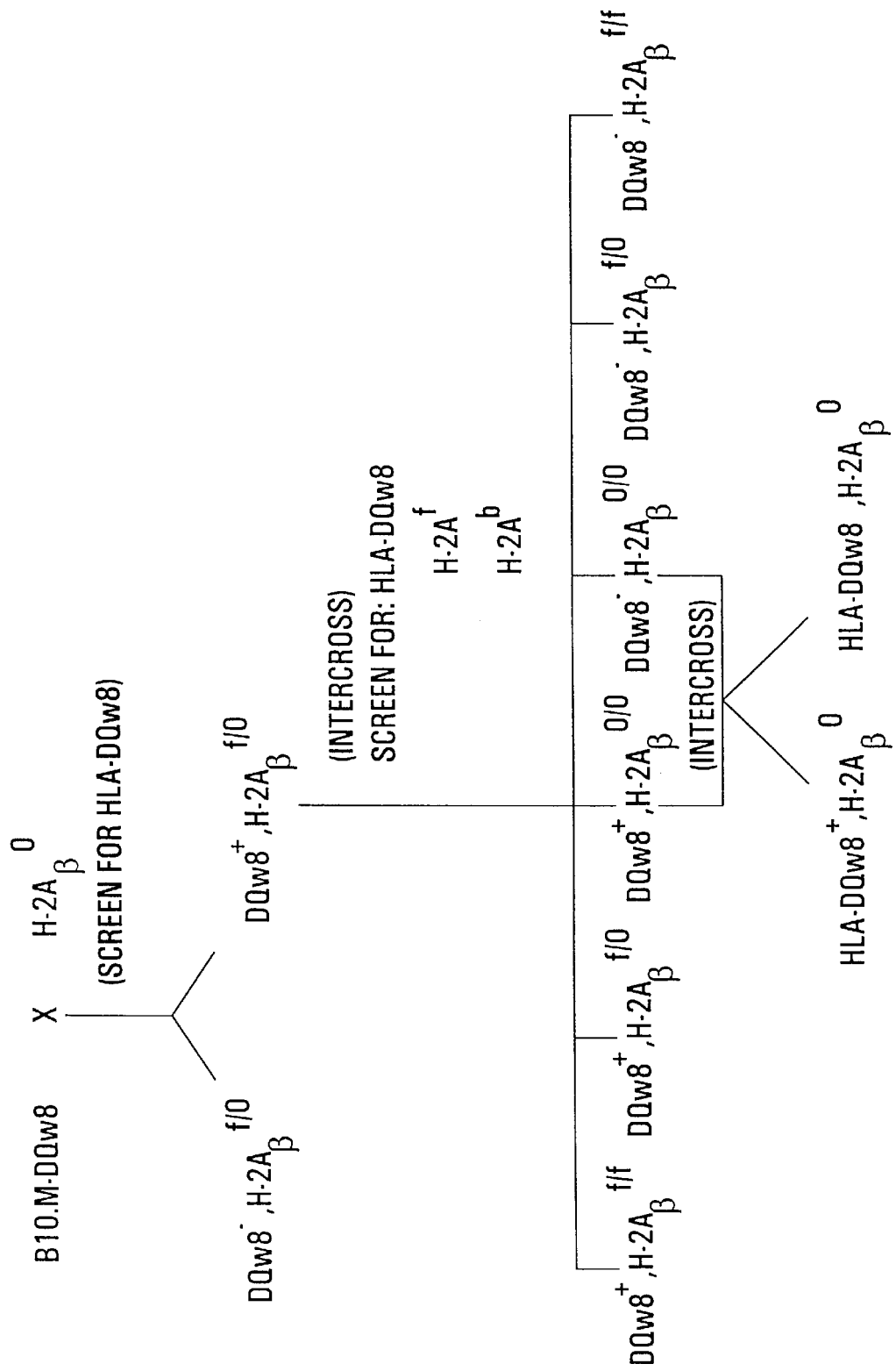

Fig. 8

| SPECIFICITIES | DETERMINANTS | DRB1 ALLELES | 67 | 70 | 71 | 74 |
|---|---|---|---|---|---|---|
| DR1/4/6 | Dw1,14,15,16,20 | 0101/0102/0404/0405/0408/0410/1402 | L | Q | R | A |
| DR2 | Dw2,12 | 1501/1502/1503/1504 | I | Q | A | A |
| DR2/5/6 | Dw5,21 | 1101/1104/1202/1305/1601 | F | D | R | A |
| DR4 | Dw4 | 0401 | L | Q | K | A |
| DR4 | Dw13,KT2 | 0403/0406/0407/0411 | L | Q | R | E |
| DR1/4/5/6 | Dw10,18,19,JVM | 0103/0402/1102/1301/1302/1304 | I | D | E | A |
| DR8 | Dw8.1,8.2 | 0801/0802/0804 | F | D | R | L |

HLA-DRBI PEPTIDES WITH SPECIFIC BINDING AFFINITY FOR HLA-DQ MOLECULES: PREVENTION AND TREATMENT OF RHEUMATOID ARTHRITIS

This invention was made with United States government support under Grant No.'s AR 30752, AI 14764 and AI 25150, awarded by the National Institutes of Health. The government has certain rights in the invention.

BACKGROUND OF THE INVENTION

Rheumatoid arthritis (RA) is a chronic inflammatory polyarthritis leading to destruction of joints and, sometimes, to severe systemic complications such as vasculitis, amyloidosis or Felty's syndrome. It is widely accepted that a strong genetic component contributes to the susceptibility or resistance to certain human autoimmune diseases such as RA. Attempts to identify the particular genes involved in these disorders has been an area of major focus for many laboratories. Among the numerous genes studied, those encoding the class I and class II molecules of the human leukocyte antigen (HLA) complex have garnered particular attention. The primary function of HLA-class I and class II molecules is binding and presentation of processed antigenic peptides to T cells bearing receptors specific for particular HLA-peptide complexes. The presentation event plays a pivotal role in shaping the cellular immune repertoire and in shaping the nature and scope of the immune response against a given antigen.

In Caucasians, genetic studies initially showed a high prevalence of certain HLA DR subtypes among RA patients. Specifically, predisposition to RA has been linked to the class 30 II HLA-DRB1 locus, and in particular to the DR4 specificity. Within the HLA-DR4 specificity, the Dw4 (DRB1*0401), Dw14 (DRB1*0404/0408), and Dw15 (DRB1*0405) subtypes confer genetic predisposition to RA, while the Dw10 (DRB1*0402) subtype does not confer such genetic predisposition. Nepom et al., *Ann. Rev. Immunol.* 9: 493–525 (1991); Wordsworth et al., *Proc. Natl. Acad. Sci. USA* 86: 10049–53 (1989); Ollier et al., *Rheum. Dis. Clin. North. Am.* 18: 741–59 (1992). Several studies have also shown that the incidence of RA is significantly decreased in patients expressing HLA-DR2 alleles compared with normal controls. Jaraquemada et al., *Ann. Rheum. Dis.* 45: 627–36 (1986); Deighton et al., Br. J. Rheumatol. 32: 893–98 (1993); Ollier et al., cited supra. Indeed, the DR2Dw12 subtype is associated with a low incidence of RA in the Japanese population. Ohta et al., *Human Immunol.* 5: 123–32 (1982). For a general review of HLA nomenclature, see Bodmer et al., *Tissue Antigens* 44: 1–18 (1994), incorporated herein by reference.

DNA sequence analysis revealed that allelic DR4 molecules mainly differ in their third hypervariable (HV3) regions. On this basis, Gregersen et al. proposed, in their "Shared Epitope" hypothesis, that sequence homologies within the HV3 regions of the RA-associated HLA-DRB1 alleles are the molecular basis for RA predisposition. Gregersen et al., *Arthritis Rheum.* 30: 1205–13 (1987); Winchester et al., *Rheum. Dis. Clin, North, Am.* 18: 761–83 (1992). In addition, the associations of Dw1 and Dw20 (DRB1*0101/0102) in several ethnic groups and Dw16 (DRB1*1402) in American Indians of the Yakima Nation with RA susceptibility further support the "Shared Epitope" hypothesis. Ollier et al., cited supra; Gregersen et al., cited supra; Winchester et al., cited supra; Willkens et al., *Arthritis Rheum.* 34: 43–7 (1991). However, associations of RA with DRB1*0301, DRB1*09011, or DRB1*1001 in Arabs, Chileans and Spaniards, respectively, do not fit this model. Ollier et al., cited supra; see also Harris, *Ann. Intern. Med.* 123: 232–33 (1995). Thus, the precise role of the "Shared Epitope" in RA susceptibility remains unknown.

A further caveat regarding studies aimed at identifying the precise HLA-D region gene responsible for susceptibility to RA is the presence of certain DQB alleles in linkage disequilibrium with particular HLA-DR genes. Such linkages further constrain any conclusions concerning the relative impact of particular HLA-D region genes on RA susceptibility. For example, two allelic forms of DQB, HLA-DQ7 and HLA-DQ8, are associated with the HLA-DR4 genotype in RA susceptibility. Gregersen et al., cited supra; Singal et al., Lancet 2: 1118–20 (1987); Lanchbury et al., *Human Immunol.* 26: 59–71 (1989). Moreover, an interesting, albeit small, study analyzing Indian patients with RA showed that 100% possessed the HLA-DQ8 allele, versus 33.3% for the normal subjects. Taneja, *Rheumatol. Int.* 11: 251–55 (1992). Thus, despite an association of the "Shared Epitope" with RA susceptibility, prior studies have also pointed to a possible role for HLA-DQ alleles in this disease.

Collagen-induced arthritis (CIA) is an experimental model of autoimmune polyarthritis that has numerous similarities to human RA. David, *APMIS* 98: 575–84 (1990). The histopathologic lesions of CIA resemble those seen in RA with synovial proliferation that progresses to pannus formation, with subsequent marginal bone erosions and cartilage destruction. Radiographs of joints affected by CIA often show erosive changes similar to those seen in human RA, and progressive arthritis often results in joint deformity and destruction similar to that seen with RA. As in some patients with human RA, anti-collagen antibodies develop in the CIA model.

In the CIA model, mice are injected intradermally with either homologous or heterologous species type II collagen with complete or incomplete Freund's adjuvant. During the first two weeks after immunization, the immune response is detected by the presence of delayed type hypersensitivity (DTH) to type II collagen as measured by skin test or ear thickness measurements. The DTH response peaks at day 10 after injection. Antibodies to type II collagen are detected in the peripheral blood 2 weeks after injection and IgG peak titers are reached at about 4 weeks. X-ray evidence of joint involvement is apparent by 4–6 weeks with the onset of clinically apparent arthritis by 7–9 weeks.

In mice, studies using congenic and recombinant mice have narrowed down the gene(s) controlling CIA susceptibility to the MHC class H-2A molecules, such that only mice with the $H-2^q$, $H-2^r$, $H-2^{w3}$ or $H-2^{w17}$ haplotypes are susceptible to the disease. Wooley et al., *J. Exp. Med.* 154: 688–700 (1981); Wooley et al., *Transplant. Proc.* 157: 180–85 (1983); Holmdahl et al., *Proc. natl. Acad. Sci. USA* 86: 9475–79 (1989). Presentation of the Type II collagen (CII) peptide 250–270 by the $H-2A^q$ molecule is probably the most important event in disease induction. Myers et al., *J. Immunol.* 151: 500–05 (1993). In q, w3 and w17 haplotypes, the H-2E molecule is not functional because of mutations in both the Ea and Eb genes. Begovich et al., *J. Immunol.* 144: 1957–64 (1990).

Thus, while human RA is associated with polymorphisms in the HLA-DRB1 locus (mouse H-2Eb equivalent), mouse CIA is associated with polymorphisms in the H-2Ab locus (human DQB1 equivalent). This presents a paradox of sorts, since to date all of the major functions of the major histocompatibility genes in humans and mice have been found to be substantially similar between equivalent regions. Resolution of this paradox would allow development of animal (e.g., mouse) models permitting identification and testing of agents for prevention and treatment of rheumatoid arthritis in humans.

SUMMARY OF THE INVENTION

The invention includes a transgenic mouse susceptible to collagen-induced arthritis, comprising a human HLA-DQ transgene representing an HLA-DQ allele associated with susceptibility to rheumatoid arthritis in humans. The transgenic mouse is deficient in functional mouse H-2 class II molecules. The transgene can be, for example, an HLA-DQ8 transgene. As used herein, the term "transgene" means an exogenous gene introduced into a mouse through human intervention, e.g., by microinjection into a fertilized egg or by other methods known to those of average skill in the art. The term includes copies of the exogenous gene present in descendants of the mouse into which the exogenous gene was originally introduced. Likewise, the term "transgenic mouse" includes the original mouse into which the exogenous gene was introduced, as well as descendants of the original mouse so long as such descendants carry the transgene.

The invention further includes a method for identifying peptides potentially effective for prevention or treatment of human rheumatoid arthritis. The method involves a) providing a transgenic mouse susceptible to collagen-induced arthritis, the mouse comprising a human HLA-DQ transgene representing an HLA-DQ allele associated with susceptibility to rheumatoid arthritis in humans, and further being deficient in functional mouse H-2 class II molecules; b) administering to the transgenic mouse a test peptide; c) after administering the test peptide, exposing lymph node cells taken from the transgenic mouse to the test peptide in vitro; and d) identifying the test peptide as potentially effective for prevention or treatment of rheumatoid arthritis if the peptide induces a proliferative response in the lymph node cells.

Alternatively, a method for identifying peptides potentially effective for prevention or treatment of human rheumatoid arthritis may comprise a) providing a test group of transgenic mice susceptible to collagen-induced arthritis, each of the mice comprising a human HLA-DQ transgene representing an HLA-DQ allele associated with susceptibility to rheumatoid arthritis in humans, and each of the mice being deficient in functional mouse H-2 class II molecules; b) providing a control group of such transgenic mice; c) administering to the test group of transgenic mice a test peptide; and d) identifying the peptide as potentially effective for prevention or treatment of rheumatoid arthritis if the test group mice exhibit reduced susceptibility to collagen-induced arthritis compared to the control group mice. By "reduced susceptibility" is meant herein that the mice exhibit a delayed onset of collagen-induced arthritis, or that the arthritis symptoms are reduced in severity, compared to the control group mice.

In either of the above-described methods, the test peptide can be an HLA-DRB1 peptide, for example an HLA-DR HV3 peptide. The HLA-DR HV3 peptide may comprise amino acids 67–74 of the HLA DR protein.

The invention further includes a method for preventing or treating rheumatoid arthritis in a patient having a rheumatoid arthritis-susceptible HLA-DQ,DR haplotype, comprising administering to the patient an HLA-DRB1 peptide having specific binding affinity for HLA-DQ molecules expressed in the patient. The HLA-DRB1 peptide may be an HLA-DR HV3 peptide, and may comprise, for example, amino acids 67–74 of the HLA DR protein. The peptides can be administered either orally or parenterally, and may be coupled to blocking agents or to carrier proteins to facilitate survival of the relevant peptide motif after administration to the patient.

The invention also includes a pharmaceutical composition for administration to a patient having a rheumatoid arthritis-susceptible HLA-DQ,DR haplotype, comprising a pharmaceutically acceptable diluent, for example a sterile, physiological saline solution, and an HLA-DRB1 peptide, the peptide having specific binding affinity for HLA-DQ molecules expressed in the patient. The peptide can be an HLA-DR HV3 peptide, and may comprise amino acids 67–74 of the HLA DR protein.

The invention further includes an article of manufacture, comprising packaging material and an HLA-DRB1 peptide within the packaging material. The HLA-DRB1 peptide has specific binding affinity for HLA-DQ molecules expressed in a rheumatoid arthritis patient. The packaging material further comprises a label or package insert indicating that the HLA-DRB1 peptide may be administered to a patient for treatment or prevention of rheumatoid arthritis.

BRIEF DESCRIPTION OF THE FIGS.

FIGS. 1A and B depicts DRB1*1502 expression on the surface of peripheral blood lymphocytes of DRB1*1502 transgene positive and negative B10.RQB3 mice, using the DRB1-specific L227 monoclonal antibody.

FIG. 2 depicts the results of a T cell proliferation assay against different concentrations of HII 250–270 peptide, expressed in Acpm (mean cpm in experimental wells—mean cpm in control wells).

FIG. 3 depicts results of a T cell proliferation assay against DRB1 peptides. Results are expressed in Δcpm (mean cpm in experimental wells—mean cpm in control wells). Values shown in the Figure are Δcpm of one representative experiment.

FIG. 4 is a schematic illustration of the generation of HLA-DQ8$^+$,H-2A$_\beta^0$ mice.

FIGS. 5A–F depicts an analysis of HLA-DQ8, murine MHC and CD4 expression in transgenic HLA-DQ8$^+$,H-2A$_\beta^0$ mice. Peripheral blood lymphocytes from HLA-DQ8$^+$, H-2A$_\beta^0$ mice (#1), Blo (#2), HLA-DQ8$^-$,H-2A$_\beta^0$ (#3) and B10.E$_\alpha^k$ (#4) animals were analyzed by flow cytometry for surface expression of the molecules HLA-DQ8 (panel A), H-2A$_\alpha^b$ (panel C), H-2E$_\beta^b$ (panel D), H-2A$_\beta^b$ (panel E) and H-2D$^b$ (panel F). The level of CD4$^+$ cells in PBL was similarly analyzed (panel B).

FIG. 6 is a graphical representation of measurements of type II collagen antibody in HLA-DQ8$^+$,H-2A$_\beta^0$ mice. Data from transgenic HLA-DQ8$^+$,H-2A$_\beta^0$ mice, negative littermate HLA-DQ8$^-$,H-2A$_\beta^0$ animals as well as control H-2A$_\beta^0$ and B10.T(6R) mice are presented.

FIGS. 7A–I presents photographs of clinical and histological presentation of collagen arthritis in HLA-DQ8$^+$,H-2A$_\beta^0$ mice. Panels A–C illustrate the appearance of a normal rear paw from a bovine CII immunized HLA-DQ8$^-$,H-2A$_\beta^0$ mouse (A) contrasted with arthritic paws from an HLA-DQ8$^+$,H-2A$_\beta^0$ animal (B) and a positive control B10.T (6R) mouse (C). Panels D-I represent cross sections of the hind foot from an arthritis-resistant HLA-DQ8$^-$,H-2A$_\beta^0$ mouse (D and G) compared with an arthritic joint from HLA-DQ8$^+$,H-2A$_\beta^0$ (E and H) and B10.T(6R) animals (F and I). The panels D and G show normal cartilage and synovial lining while the panels E, F. H and I show regions of mononuclear cell infiltration of the synovium with pannus formation and cartilage and subchondral bone erosions. The magnifications of each section are noted in the lower right hand corner. The areas of tissue illustrated in panels G, H and I are higher magnifications of the boxed areas in panels D, E and F respectively.

FIG. 8 depicts the polymorphic residues at positions 67, 70, 71 and 74 of the HV3 region of HLA-DRB1 molecules. The residues are listed using the one-letter amino acid code, where A=Ala, D=Asp, E=Glu, F=Phe, I=Ile, K=Lys, L=Leu, Q=Gln, R=Arg. The region 65–79 covering this polymorphic region constitutes the seven DRB1 HV3 peptides used in the present study. They are referred to herein, from top to bottom, as Dw14, Dw2, Dw21, Dw4, Dw13, Dw10 and Dw8.1 respectively.

FIGS. 9A–B depicts the response of HLA-DQ8,H-2A$_\beta^0$ mice to Dw10 HV3 peptide (65–79). Panel (A) summarizes data demonstrating that the response is dose-dependant. Panel (B) summarizes data demonstrating that the response is HLA-DQ-restricted and driven by CD4$^+$CD8-negative T cells. The values are expressed in Acpm (mean cpm in experimental wells—mean cpm in control wells without peptide).

FIG. 10 depicts the results of a T cell proliferation assay using cells from HLA-DQ8,H-2A$_\beta^0$ mice immunized with the seven DRB1 HV3 peptides listed in FIG. 8.

DETAILED DESCRIPTION

Figure 1A:
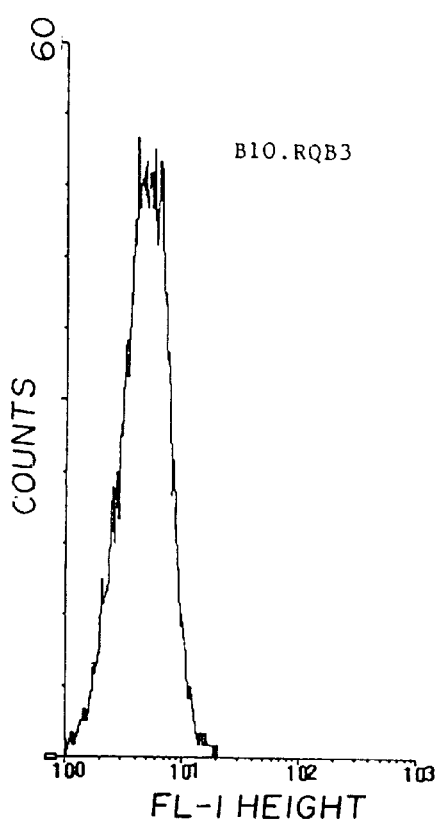

To determine whether or not H-2E (HLA-DR equivalent) molecules in fact play a role in CIA (i.e., to further explore the apparent paradox described above), the present inventors performed experiments with mice from the B10.RQB3 (Ab$^q$, Aa$^q$, Eb$^o$, Ea$^k$) strain. This strain of mice expresses the H-2A$^q$ molecule and possesses a functional Ea$^k$ gene, but does not have an intact H-2E molecule since the Eβ chain is absent due to a non-functional Eb$^q$ gene. These mice are CIA susceptible due to the redisposing H-2A$^q$ molecule. Transgenic mice were generated using the entire Eb$^d$ gene, and mated with B10.RQB3 mice resulting in expression of a functional Eβ$^d$/Eα$^k$ molecule on the cell surface. These mice showed a significant decrease in both incidence and severity of CIA. The protective effect of the Eβ$^d$ molecule on CIA was confirmed using a second line of transgenic mice generated with a 10.2 Kb DNA construct containing only 200 bp of promoter region. No significant difference was found in the Vβ usage between Eb$^{d+}$ and Eb$^{d-}$ littermates, thus ruling out specific Vβ-bearing T-cell deletions as an explanation for this protective phenomenon. Next, a series of F$_1$ crosses was set up between B10.RQB3 and congenic mice with different H-2 haplotypes, in order to assess whether or not Eb gene polymorphisms might influence the protective effect of the H-2E molecule on CIA. Of the Eβ$^{b,d,k,p,s}$ polymorphisms, only Eβ$^d$ was confirmed to have a protective role. Of the other Eβ molecules, only Eβ$^s$ was associated with a partial protection. Thus, Eb gene polymorphisms definitely can determine protection from CIA.

In a further set of experiments, B10.Q (H-2A$^q$) mice were immunized with peptides 65–79 covering the HV3 region of the Eβ$^d$ or Eβ$^s$ molecules. Lymph node cells from the immunized animals proliferated in response to these peptides. Similar results using B10.RQB3 mice confirmed the presentation of Eβ$^d$ and Eβ$^s$ peptides by H-2A$^q$ molecules. Conversely, Eβ$^{b,k}$ and Eβ$^p$ peptides failed to induce T-cell proliferation using B10.RQB3 lymph node cells. Therefore, a correlation exists between T-cell proliferation to HV3 peptides 65–79 and protection of the corresponding H-2E molecules against CIA.

Interestingly, the introduction of the Ebd transgene did not induce tolerance to the same self-peptide, suggesting that Eβ$^d$-specific T cells have not been deleted and can be activated. Similarly, (B10.RQB3×B10.RDD)F$_1$ mice responded to the Eβ$^d$ 65–79 self-peptide. Even more striking is the correlation between failure of the Ebd transgene to protect CIA-susceptible B10.RIII (H-2$^r$) mice and the lack of T-cell proliferation of B10.RIII lymph node cells when challenged with Eβ$^d$ peptide 65–79. Thus, the H-2Ar molecule not only presents an arthritogenic CII peptide to induce autoreactivity, but also fails to present a potentially protective Eβ peptide in these animals.

On the basis of these results, it was possible to hypothesize that the HV3 regions of protective forms of mouse Eβ molecules might, themselves, constitute antigenic peptides capable of binding to CIA-susceptible forms of the mouse H-2A molecule, thereby mediating the protective effect. Extensive additional investigations with human genes were required to establish a correlation with the human situation, i.e, that the homologous genes H-2A in the mouse and DQ in the human are the susceptibility genes for rheumatoid arthritis, and that the homologous genes H-2E in the mouse and HLA-DR in the human are the protective genes for rheumatoid arthritis. To this end, the present inventors have performed an extended series of experiments with transgenic mice carrying human DQ and DR genes.

In a first set of experiments (see EXAMPLE 1, below), a human DRB1*1502 (DR2Dw12) transgene was introduced into CIA-susceptible B10.RQB3 (H-2A$^q$) mice. Transgene-positive DRB1*1502 mice displayed a significant reduction in the incidence and severity of arthritis. T cells from the transgene-positive mice were dramatically less responsive to an arthritogenic type II collagen peptide than were T cells from control mice. In addition, the clinical reduction in arthritis incidence and severity correlated with the T cell proliferative response of the B10.RQB3-DRB1*1502 mice against a self-derived DRB1 peptide from the third hypervariable region (HV3).

This appears to be the first example of protection in an experimental model of autoimmune disease afforded by a human DRB1 transgene that has been negatively associated with rheumatoid arthritis. The present results provide critical evidence that self-MHC derived peptides modulate the presentation of autoantigenic determinants such as Type II collagen peptides. The results also implicate the H-2A$^q$-homologous HLA-DQB1 and DQA1 loci as the actual arthritis-predisposing human loci in the HLA class II region.

To further investigate this phenomenon, a second set of experiments (EXAMPLE 2, below) were directed to expression of an RA-associated human HLA-DQ8 molecule in class II-deficient mice. Transgenes encoding the α and β molecules of the RA-associated HLA-DQ8 molecule were introduced into mouse class II deficient H-2A$_\beta^0$ mice. These mice were then evaluated for susceptibility to CIA. The HLA-DQ8+,H-2A$_\beta^0$ mice displayed good expression of the human HLA-DQ8 molecule while no surface expression of endogenous murine class II molecule could be detected. In addition, the HLA-DQ8 molecule induced selection of CD4$^+$T cells expressing a normal repertoire of V$_\beta$ T cell receptors (TCR). Immunization of the HLA-DQ8$^+$,H-2A$_\beta^0$ mice with bovine type II collagen (CII) induced a strong antibody response that was cross-reactive to homologous mouse CII. Importantly, the anti-CII response was arthritogenic; a severe polyarthritis developed in a majority of the HLA-DQ8$^+$,H-2A$_\beta^0$ mice that was indistinguishable from the polyarthritis seen in the arthritis-susceptible B10.T(6R) (H-2A$^q$) controls.

These experiments represent the first demonstration that a pathogenic autoimmune response in mice can be generated by expression of a human MHC class II molecule. The data clearly demonstrate that expression of the HLA-DQ8 molecule confers susceptibility to CIA. The results further point to a functional synergy between particular HLA-DQ alleles and HLA-DR molecules possessing the "shared epitope," and implicate these molecules as co-requisite factors in the development of RA. The HLA-DQ8$^+$,H-2A$_\beta^0$ mice generated in this study represent a novel model to study autoimmune arthritis, and provide useful vehicles to assess the therapeutic efficacy of human HLA class II blocking agents in modulation of a pathogenic in vivo immune response.

To this end, the present inventors investigated the antigenicity of peptides from the HV3 regions of RA-associated and non-associated human DRB1 molecules in the above-described HLA-DQ8,H-2A$_\beta^0$ transgenic mice (see EXAMPLE 3, below). Seven DRB1 HV3 peptides, covering region 65–79, were synthesized. These peptides represented all the DR1 and DR4 subtypes, most of the DR2 and DR8 subtypes, and some of the DR5 and DR6 subtypes. Thus, some of the peptides are carried by HLA haplotypes associated with RA predisposition, while others are carried by HLA haplotypes that have not been associated with RA.

The HLA-DQ8 transgenic mice were immunized with the synthesized peptides. Strikingly, only DRB1 HV3 peptides derived from RA-associated DRB1 allelic chains, i.e., Dw4, Dw13 and Dw14 peptides, failed to induce proliferation in vitro of T cells from the HLA-DQ8 transgenic mice. The data therefore confirm a correlation between an ability of T cells from HLA-DQ8,H-2A$_\beta^0$ mice to proliferate against DRB1 HV3 peptides and the non-association of the corresponding HLA-DR subtypes with RA predisposition.

The lack of response to the Dw13 HV3 peptide raises a question, since some studies have associated the Dw13 subtype with low incidence of arthritis. However, unlike Dw10, the Dw13 haplotype can carry either HLA-DQ8 (DQB1*0302) or HLA-DQ7 (DQB1*0301) alleles. Most of the studies associating the Dw13 subtype with low incidence of arthritis have failed to indicate which DQ allele was linked to the DRB1*0403, B1*0406, B1*0407 or B1*04011 alleles. In Polynesians where HLA-DQ8 is predominant (Gao and Serjeanston, *Hum. Immunol.* 32: 269–76 (1991)), the frequencies of the Dw13 subtype in RA patients and healthy subjects are similar, and the relative risks for developing RA in both Dw13 and Dw4 individuals are nearly identical. Tan et al., *Arthritis Rheum.* 36: 15–19 (1993). Thus, the lack of proliferative response found in HLA-DQ8, H-2A$_\beta^0$ mice using Dw13 HV3 peptide suggests that only Dw13 individuals who carry the DQ7 allele are not predisposed to RA.

HLA class II-derived peptides constitute a major fraction of naturally processed peptides bound to HLA class II molecules. Vogt et al., *J. Immunol.* 153: 1665–73 (1994); Chicz et al., *Int. Immunol.* 6: 1639–49 (1994); Hunt et al., *Science* 256: 1817–20 (1992); Urban et al., *Chem. Immunol.* 57: 197–234 (1993). If the Dw2, Dw8.1, Dw10 and Dw12 HV3 peptides are naturally processed antigenic peptides, it is likely that they fit into the groove of the HLA-DQ8 molecule. This is indicated by the results of the present investigations, which clearly demonstrate that a lack of T cell proliferation of HLA-DQ8,H-2A$_\beta^0$ mice against HV3 DRB1 peptides correlates with RA predisposition defined by DRB1 polymorphisms represented in Dw1,4,14,15 and 16 subtypes. Thus, both HLA-DR and HLA-DQ alleles influence disease susceptibility and protection.

While the present invention is not limited by a particular mechanism of action, it is possible to postulate feasible mechanisms to account for the protective effect of DRB1 peptide binding to DQ molecules. First, DRB1 peptides may act as "endogenous competitors" that modulate the binding of a second antigenic peptide, for example potential autoantigens, to DQ molecules. This model is compatible with both the mechanism of peptide exchange proposed by Adorini et al., *Nature* 342: 800–03 (1989), as well as a model where peptide binding to a class II molecule is dependent on a two-peptide, class II-intermediate stage. De Kroon and McConnell, *J. Immunol.* 152: 609–19 (1994). An alternative, more active mechanism is one in which the binding of self-derived MHC peptides to class II molecules modulates disease predisposition through induction of antigen-specific regulatory cells. Wauben et al., *J. Exp. Med.* 176: 667–77 (1992). This is reminiscent of the model proposed by Nishimura et al., *Res. Immunol.* 142: 459–66 (1991), where some HLA-DQ-restricted CD4$^+$T cells are involved in low responsiveness to some natural antigens and that autoimmune disease-associated HLA-DQ alleles may not induce "immune suppression" to autoantigens.

The information revealed by the present experiments enables design of peptide-based treatments and vaccines for individuals at risk for developing RA or who are afflicted with RA. Moreover, the fundamental molecular genetic mechanisms uncovered by the present inventors will undoubtedly have relevance to other autoimmune disorders with known HLA class II genetic association.

To identify human peptides effective or potentially effective for prevention or treatment of rheumatoid arthritis, selected peptides representing portions of HLA-DRB1 molecules (HLA-DRB1 peptides) are synthesized and purified according to standard methods. These peptides are then tested for binding to HLA-DQ molecules through use of mice possessing functional human HLA-DQ transgenes but lacking functional mouse H-2 class II molecules. For example, the HLA-DQ8,H-2A$_\beta^0$ mice described above and in the following Examples may be administered a preparation of peptide comprising 10–1000 µg, preferably about 100 µg, of peptide in a saline solution and Complete Freund's adjuvant. Administration can be by injection into the tail or by other routes of administration known to the average skilled artisan (e.g., into the rear footpads). After an appropriate interval post-immunization, generally about one week, lymph node cells are isolated and challenged in vitro with varying concentrations of the corresponding peptide. Those peptides inducing a significant dose-dependent lymphocyte proliferative response that is HLA-DQ-restricted are selected for further study.

The selected peptides are administered to transgenic mice as described above, i.e., mice possessing functional human HLA-DQ transgenes but lacking functional mouse H-2 class II molecules. For example, peptides can be dissolved in an appropriate saline solution and administered intravenously to HLA-DQ8,H-2A$_\beta^0$ mice. Generally, an adjuvant is not included in the administered injectate. The transgenic mice are administered type II collagen and adjuvant under conditions that would normally lead to development of CIA. The selected peptides are administered prior to, concomitant with, or after administration of the type II collagen, and the mice are monitored for symptoms of CIA. Peptides that engender a delayed onset or a reduced severity of CIA are targeted for further study in a clinical setting.

In an alternative embodiment, the peptides are administered to the transgenic mice by an oral route. In both humans and mice, it is thought that orally administered peptides enter from the intestinal lumen into lymphatics and are carried to draining mesenteric lymph nodes, where various immune interactions occur. Some ingested peptides may be transported via M cells into Peyer's patches, where they are able to engender responses from both T and B lymphocytes. Lymphocytes that are activated in mesenteric lymph nodes may migrate to the lamina propria. Lymphocytes stimulated in Peyer's patches may also migrate to the lamina propria, or into mesenteric lymph nodes and, finally, into the general circulation. Thus, orally administered peptides may gain access to, and engender responses in, the mucosal immune system and the rest of the immune system. See, e.g., Abbas et al., *Cellular and Molecular Immunology*, 2nd Ed., W. B. Saunders Company 1994, pages 233–235; Chen et al., *Nature* 376: 177–180 (1995).

For oral administration, the peptides are dissolved in saline, without adjuvant, and fed to selected mice (e.g., HLA-DQ8,H-2Ahd β° mice), preferably by gastric intubation using a 21G ball tipped animal feeding needle. The mice may be fed with various concentrations of peptide and for various lengths of time. In one embodiment, the mice are fed with a selected amount, for example 100 μl (1 mg/ml), of peptide every other day for a period of 20 days. This is followed, two days after the last peptide dose, by immunization with type II collagen to induce CIA. Alternatively, the animals may be first immunized to induce arthritis on day 0, prior to peptide administration. Mice are then orally fed peptide from about 20 to about 45 days post-immunization with a selected amount, for example 100 μg, of peptide every other day. Various other combinations of peptide and type II collagen administration protocols may be used as appropriate to particular peptide preparations and mouse strains. Such routine variations in protocol will be apparent to the average skilled artisan.

Following administration of the relevant peptides and the type II collagen, the mice are monitored two to three times per week for onset and severity of arthritis. Generally this monitoring is performed for a period of from about 3 to about 16 weeks. Severity of arthritis is assessed by monitoring joint involvement; this can be manifested, for example, in redness or swelling in the paws or toes, severe swelling or joint deformity, and joint ankylosis. The symptoms can be worked into a grading system of severity that is applicable to individual limbs. The scores for each limb can be summed to provide a severity score for each animal. Arthritis incidence and severity can be compared between experimental groups using appropriate statistical analyses known to the skilled artisan, for example the $X^2$ test with Yates' correction and the non-parametric Mann-Whitney U test.

Human HLA-DRB1 peptides demonstrating anti-CIA activity in the transgenic mice are useful for treatment of, and testing in, human patients. The peptides can be administered to human patients either by oral administration or parenteral administration (e.g., intravenous injection). The peptides generally are administered without an adjuvant. Preferably the peptides are administered in an appropriate physiological saline solution, although any appropriate carrier solution known to the skilled artisan may be used for administration.

In an alternative embodiment, the peptides can be coupled, at either or both of the amino- and carboxyl-terminal residues, with a blocking agent in order to facilitate survival of the relevant peptide motif in vivo. This can be useful in those settings in which the peptide termini tend to be degraded ("nibbled") to one degree or another prior to cellular uptake or binding to HLA-DQ molecules. Such blocking agents can include, without limitation, additional related or unrelated peptide sequences that can be attached to the amino- and/or carboxyl-terminal residues of the HLA-DRB1 peptide to be administered. Alternatively, blocking agents such as pyroglutamic acid or other molecules known to those of average skill in the art may be attached to the amino- and/or carboxyl-terminal residues of the HLA-DRB1 peptide. For similar reasons, the peptides can be coupled to pharmaceutically acceptable "carrier" proteins prior to administration.

The peptides may be administered to presymptomatic patients at risk for developing rheumatoid arthritis to delay or prevent the onset of clinical disease. Such patients can include, without limitation, individuals having HLA-DR and HLA-DQ haplotypes associated with susceptibility to rheumatoid arthritis as described herein. Alternatively, the peptides may be administered to patients displaying clinical symptoms of rheumatoid arthritis to delay or prevent continued deterioration, or to effect improvement in the existing condition. The peptides administered to human patients have specific binding affinity for HLA-DQ molecules expressed in the patients. In a preferred embodiment, the peptides are derived from the HV3 regions of human HLA-DRB1 molecules. Such peptides may consist of or include amino acids 67–74 of the HLA DR HV3 region. The administered peptides may be a single species of peptide, or may include a "cocktail" of various peptides identified as useful for prevention or amelioration of rheumatoid arthritis in particular patients.

The following examples are offered by way of illustration and are not intended to limit the invention in any manner.

EXAMPLE 1

Introduction of a Protective Human HLA-DRB1 Transgene into CIA-Susceptible Mice

A. MATERIALS AND METHODS

Mice. The mice employed in these studies were bred and maintained in the pathogen-free Immunogenetics Mouse Colony of the Mayo Clinic.

Generation of B10.RQB3-DRB1*1502 transcenic mice. DRB1*1502 transgenic mice were generated by microinjecting a linearized 34 Kb DNA fragment containing the entire DRB1*1502 gene, isolated from the HLA-homozygous B cell line AKIBA (DR2, Dw12, DQw6) (see Kawai et al., J. Immunol. 142: 312–17 (1989)) into (SWR x B10M)F$_2$ fertilized eggs. DRB1*1502 positive founders were identified by polymerase chain reaction using the primers (5'-C(CT)TAAGAGGGAGTGTCATTTCTTC3') (SEQ ID NO: 1) and (5'TGTGAAGCTCTC(AC)(AC)CAACCCC-3') (SEQ ID NO: 2), located in the second DRB1 exon. The DRB1*1502 transgene was introduced into the B10.RQB3 (Aa$^q$ Ab$^q$ Eb$^q$ Ea$^k$) mice by crossing with the founder mouse. Those offspring of this cross who were positive for the transgene were backcrossed for ten generations. The B10.RQB3 mice express the CIA susceptible H-2Aq molecule but lack H-2E expression since their Eb$^q$ gene is mutated. The DRB1*1502 molecule is expressed on the cell surface by pairing of the DRB1*1502 molecule with the Ea$^k$ molecule, which is highly homologous to the DRα molecule.

Flow cytometry. Peripheral blood lymphocytes were isolated by Ficoll separation, washed and incubated with the DRB1-specific monoclonal antibody L227 (Grumet et al., *J. Immunol.* 125: 2785–89 (1980)) for 30 min. at 4° C. Later, the cells were washed and incubated with FITC goat anti-mouse IgG (Accurate Chemical and Scientific Corp., Westbury, N.Y.) for 30 min. at 4° C., washed and fixed with 1% paraformaldehyde before analysis. Single color flow cytometric analysis for DRB1*1502 expression using the L227 monoclonal antibody was performed by a FACSRIV flow cytometer (Becton Dickinson & Co., Mountain View, Calif.).

Induction and quantification of arthritis. Eight to 12 week-old B10.RQB3-DRB1*1502 mice along with congenic B10.RQB3 controls were immunized with a cold emulsion of bovine type II (BII) collagen in complete Freund's adjuvant (CFA), as previously described. Gonzalez-Gay et al., *J. Exp. Med.* 180: 1559–64 (1994). Briefly, BII was dissolved in 0.1M acetic acid at a concentration of 2 mg/ml, then emulsified 1:1 with complete Freund's adjuvant H37 Ra (Difco Laboratories, Detroit, Mich.). Eight to twelve week-old mice were intradermally injected with 100 μg of the emulsion in the root of the tail and then monitored for the onset and development of arthritis from the third to the ninth week postimmunization. Arthritic severity of all the limbs was determined as described in Wooley et al., *J. Exp. Med.* 154: 688–700 (1981) using a scale from 0 to 3 for each paw, where; 0=no arthritis; 1=redness and swelling in the paw or toes; 2=severe swelling or deformity in the paw; and 3=ankylosis. An arthritic score for each mouse was obtained by summing the score in each paw. Thus, the possible severity as measured by the arthritic score ranged from 0 to 12. Animals were followed for the onset and severity of arthritis from the third to the ninth week postimmunization. Incidence and severity of arthritis did not change after the ninth week postinjection. Arthritis score was calculated at the end of the study considering only arthritic mice.

Measurement of serum Anti-Collagen type II-specific antibody. Sera from mice bled at the fifth week postimmunization were tested at 1:100 and 1:400 dilutions using a standard ELISA specific for type II collagen as previously described. Gonzalez-Gay et al., *J. Exp. Med.* 180: 1559–64 (1994). Sera to determine anti-BII and anti-mouse type II (MII) antibodies were compared to a pooled positive control serum. Results are shown as mean optical density (O.D.) ±S.D.

Peptide synthesis. Peptides covering the sequences 65–79 of the HV3 region of DRB1*1502 (DR2Dw12) and DRB11601(DR2Dw21) were chemically synthesized by a solid phase procedure by using an Applied Biosystem synthesizer as previously described. Krco et al., *Transplantation* 54: 920–23 (1992). The sequences of these DR2 peptides, using the standard one-letter code, are the following:

DRB1*1502 65–79: K-D-I-L-E-Q-A-R-A-A-V-D-T-Y-C (SEQ ID NO: 3)

DRB1*1601 65–79: K-D-F-L-E-D-R-R-A-A-V-D-T-Y-C (SEQ ID NO: 4)

An immunodominant peptide (HII 250–270) of human type II collagen was similarly synthesized as previously described by Krco et al., cited supra. This peptide has been previously recognized as a T cell epitope in arthritis susceptible H-2$^q$ mice. Khare et al., *FASEB J.* 8: A967 (1994). The sequence of HII 250–270 is as follows: G-P-K-G-Q-T-G-K-P-G-I-A-G-F-K-G-E-Q-G-P-K (SEQ ID NO: 5).

T cell proliferation assay. B10.RQB3-DRB1*1502 positive and negative littermates were injected with 200 μg of HII 250–270 peptide emulsified in CFA. Ten days later, draining lymph nodes were removed and tested in vitro for lymphocyte proliferation assay. One hundred μl of cells at a concentration of 1×10$^7$/ml were cultured for 48 hours with HII 250–270 peptide at 4 μg/ml, 20 μg/ml, and 100 μg/ml as described in Krco et al., cited supra. In the same experiments, purified protein derivative from Mycobacterium Tuberculosis (PPD)(20 μg/ml), lipopolysaccharide (LPS) (40 μg/ml) and Concanavalin A (Con A) (10 μg/ml) were used as controls. Results were expressed in ACPM (mean CPM in experimental wells—mean CPM in the control wells). Similarly, B10.RQB3-DRB1*1502 positive and negative littermates and B10.RIII (H-2r) mice were immunized with peptides covering the region 65–79 of the DRB1*1502 or DRB1*1601 molecules. Seven days later, cells from draining lymph nodes were removed and tested in vitro against the same peptides, as described in Khare et al., cited supra.

Statistical analysis. Arthritis incidence between B10.RQB3-DRB1*1502 mice and B10.RQB3 controls was compared using Chi square test with Yates' correction. The Student's t-test was employed to analyze antibody levels.

B. RESULTS

Figure 1B:
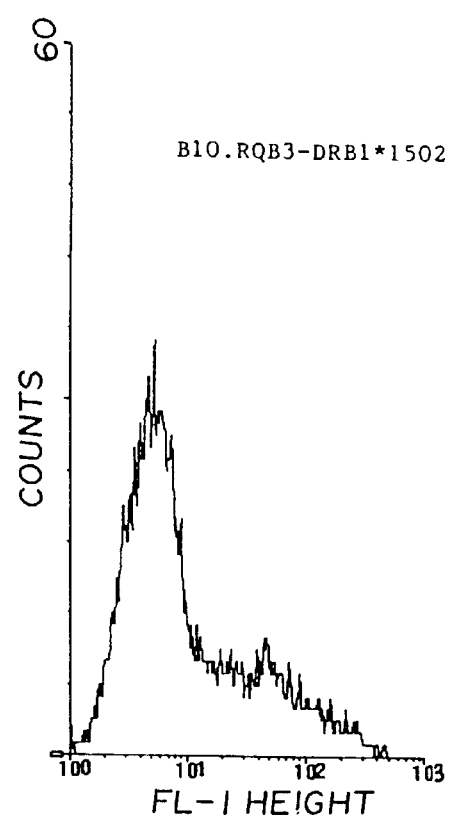

The HLA-DRB1*1502 (DR2Dw12) molecule protects mice from arthritis. The DRB1*1502 chain was able to pair with the Eα$^k$ chain as measured by cell surface expression since DRα and Eα chains are highly homologous (Grummet et al., *J. Immunol.* 125: 2785–89 (1980); see also FIG. 1). This is in agreement with results previously published by Lawrence et al., *Cell* 58: 583–94 (1989), showing that an HLA-DRa transgene can restore H-2E expression. The percentage of PBLs expressing the DRB1 chain was 41.4±3.2% for B10.RQB3-DRB1*1502 mice versus 3.0±0.9% for the negative littermates.

To evaluate the effect of the DRB1 transgene on CIA, B10.RQB3 controls and congenic B10.RQB3-DRB1*1502 mice were immunized with BII in CFA. At 9 weeks postimmunization, B10.RQB3-DRB1*1502 animals showed a significant reduction in the incidence of CIA (9 out of 30, 30%) compared to B10.RQB3 controls (19 out of 23, 83%) ($p<0.001$, Table 1). The arthritic score in the 9 B10.RQB3-DRB1*1502 mice showing clinical signs was reduced (1.7±1.0 versus 3.8±1.5 in the B10.RQB3 controls, Table 1). Also, only 1 out of 9 B10.RQB3-DRB1 1502 mice that developed CIA had severe arthritis while in the others the extent of arthritis was mild and the arthritic scores ranged between 1 and 2. Arthritis in the controls was very severe involving ankylosis and deformity in most of the animals. Furthermore, onset of arthritis was also delayed in B10.RQB3-DRB1*1502 animals compared to controls. Finally, anti-MII antibody titers in the sera of B10.RQB3-DRB11502 mice were half the control animals (Table 1). The results remained unchanged from the ninth week to the termination of the experiments at 12 weeks.

TABLE 1

Protection against CIA in B10.RQB3-DRB1*1502 transgenic mice

| | CIA† | | | Antibody titers‡ | |
|---|---|---|---|---|---|
| | | | Severity | | |
| Mice | Incidence | (%) | mean ± SD | BII | MII |
| B10.RQB3-DRB1*1502 | 9/30§ | (30) | 1.7 ± 1.0 | 0.45 ± 0.15 | 0.24 ± 0.11' |
| B10.RQB3 controls | 19/23§ | (83) | 3.8 ± 1.5 | 0.60 ± 0.14 | 0.52 ± 0.15' |

*Mice were immunized with 100 μg of BII in Complete Fruend's adjuvant on day 0 and monitored regularly for the onset and development of CIA.
†Determined at 9 week postimmunization. The mean severity of arthritis was calculated using arthritic mice only.
‡Mice were bled at 5 week postimmunization and the level of antibody against BII and MII determined by a standard ELISA. Data are presented as the mean OD at 1:100 dilution. Arthritis incidence between groups was compared using $\chi^2$-test with Yates' correction. Antibody levels were studied using the Student's τ test.
§$p < 0.001$, '$p < 0.01$.

The pairing of Eak to ES molecules such as E$\beta^p$, E$\beta^b$ or E$\beta^k$ does not lead to protection in CIA (data not shown). Thus, this protection is not related to expression of the E$\beta^k$ molecule. There was also no difference in the V$\beta$-specific T cell receptor (TCR) repertoire between the B10.RQB3-DRB1*1502 and the B10.RQB3 controls (data not shown). This was not surprising since the parental B10.RQB3 is known to delete TCR VS-specific T cells through the presentation of mammary tumor virus superantigen by interisotypic A$\beta^q$/E$\alpha^k$ heterodimers. Anderson et al., *J. Exp Med.* 170: 1003–08 (1989).

Lymphoproliferative response to type II collagen peptide 250–270. Both T and B cells are involved in pathogenesis of CIA. As disclosed above, the autoantibody response to MII in the B10.RQB3-DRB1*1502 mice was significantly reduced. Next, T cell response against a T cell epitope of type II collagen was tested both in B10.RQB3-DRB1*1502 positive and negative littermates. B10.RQB3-DRB1*1502 positive and negative littermates were immunized with the immunodominant arthritogenic peptide HII 250–270. When T cells from B10.RQB3-DRB1*1502 and B10.RQB3 control mice were challenged in vitro with various concentrations of HII 250–270, a dramatic reduction in the T cell response of DRB1*1502 transgene positive animals, only, was observed, especially at lower concentrations of peptides (FIG. 2). Conversely, T cell proliferation against PPD (a constituent of CFA), as well as proliferation against LPS and Con A, was similar using transgene positive and negative littermates (data not shown). Therefore, it may be concluded that the impaired response to HII 250–270 in DRB1*1502 mice is antigen-specific and is related to protection against arthritis.

Two explanations may account for these results. One is that DRB*1*1502/E$\alpha$ dimers may be competing with the H-2A$^q$ molecule for binding to HII 250–270 peptide. However, no evidence for HII 250–270 peptide presentation by the DRB1*1502 molecule was found (data not shown). An alternative explanation is that peptides derived from the DRB1*1502 molecule bind to the A$\beta^q$ molecule and interfere with the binding of arthritogenic peptide(s).

Figure 3:
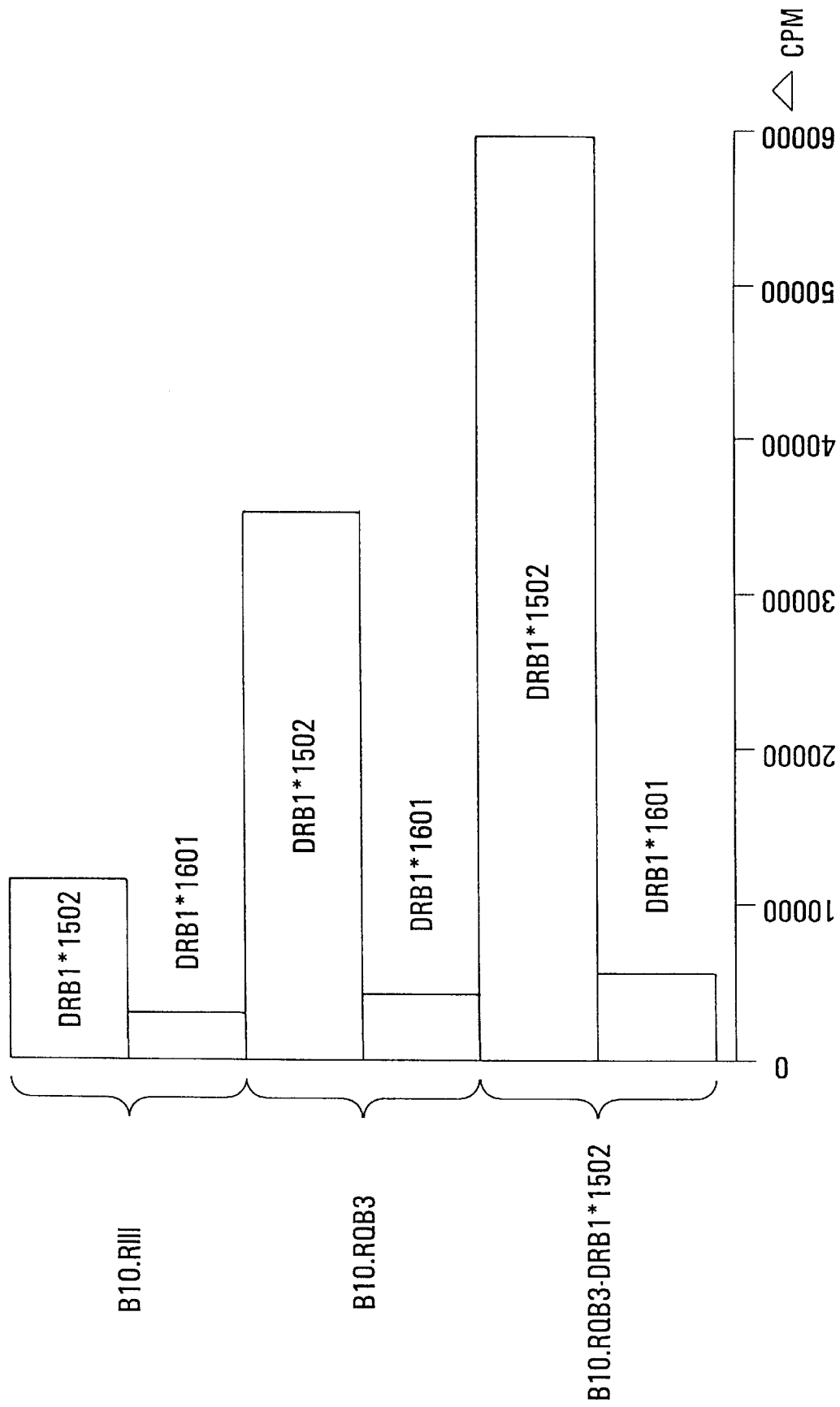
Figure 5A:
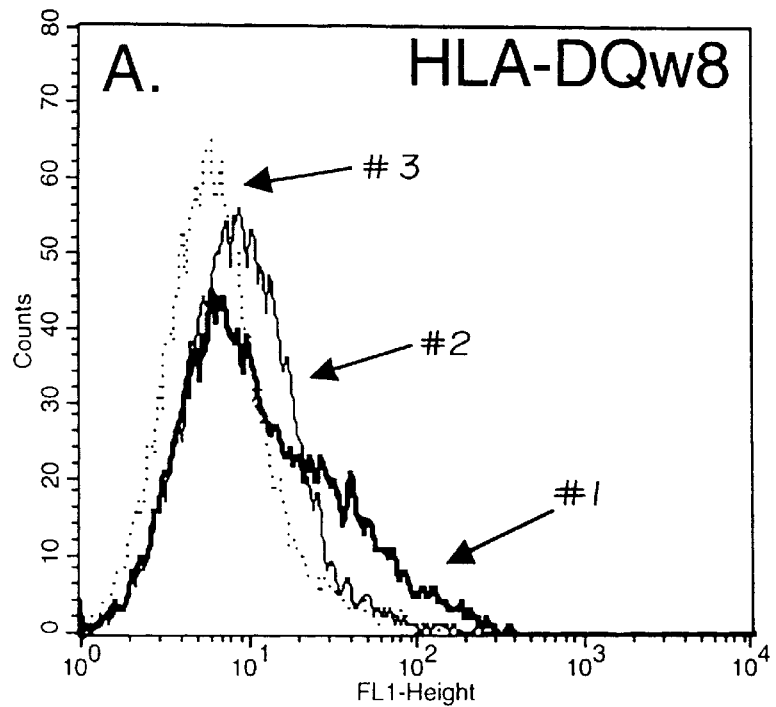
Figure 5B:
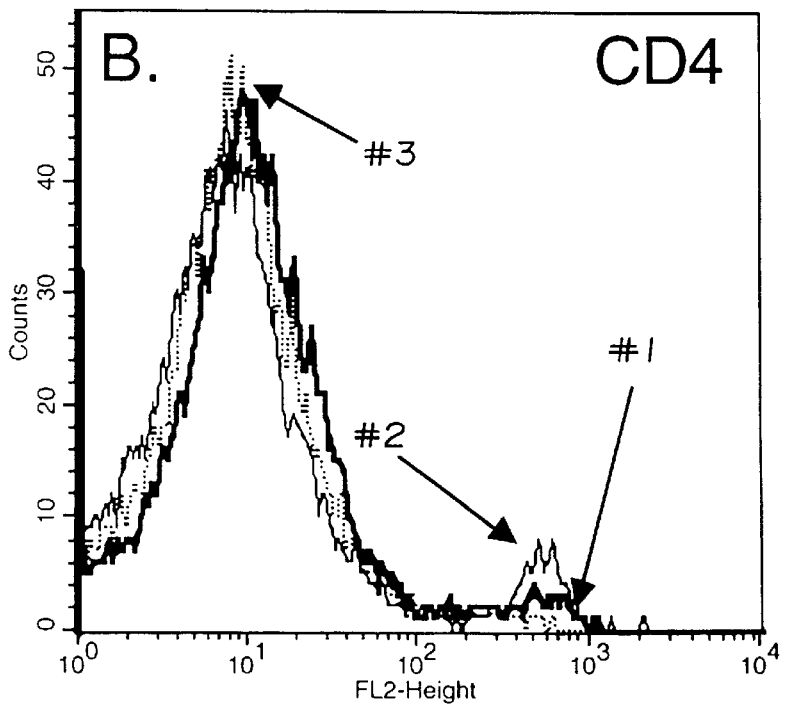
Figure 5C:
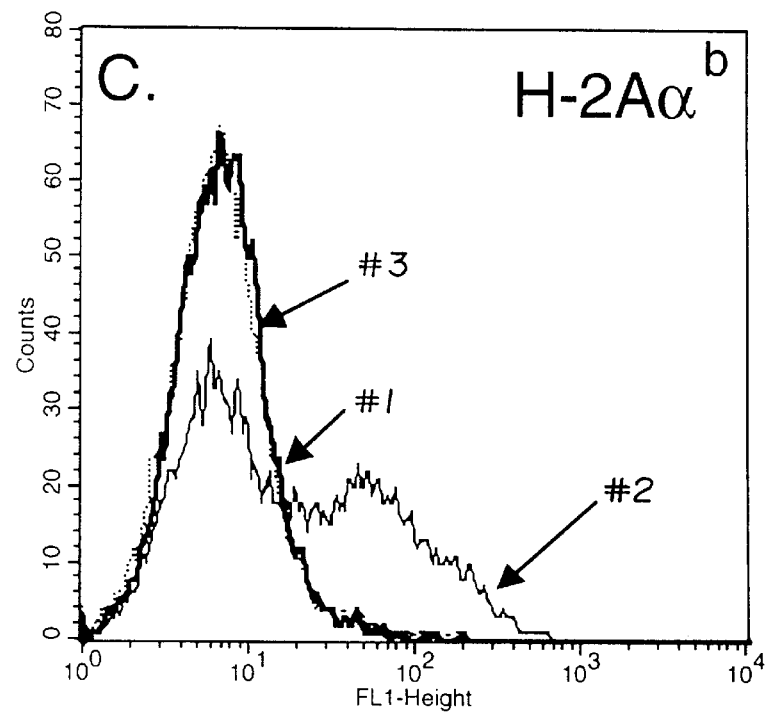
Figure 5D:
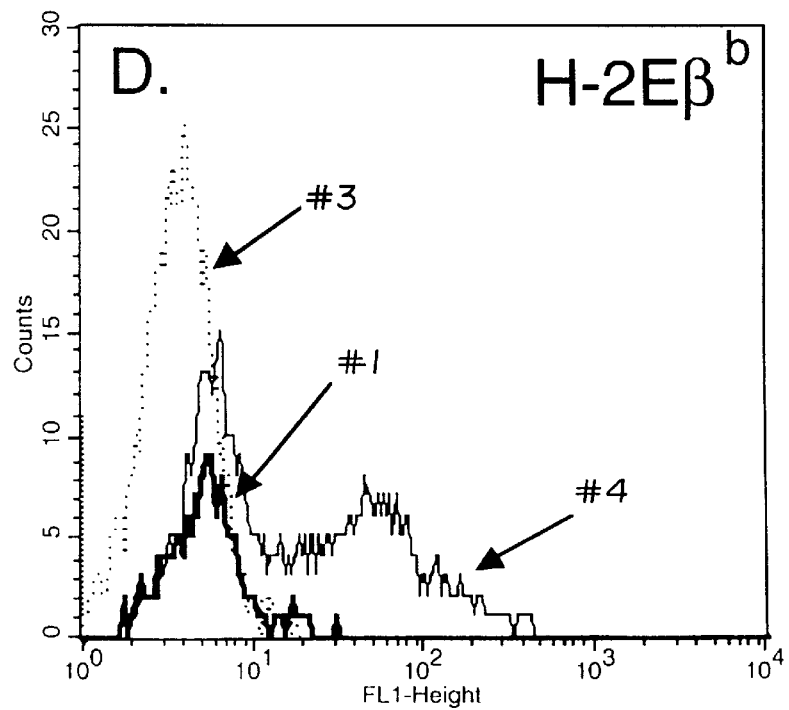
Figure 5E:
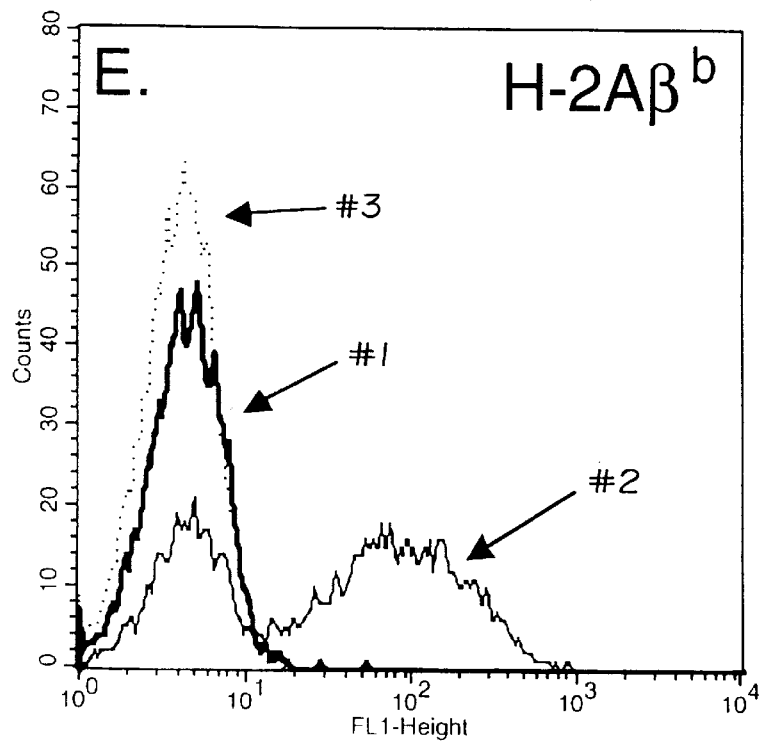
Figure 5F:
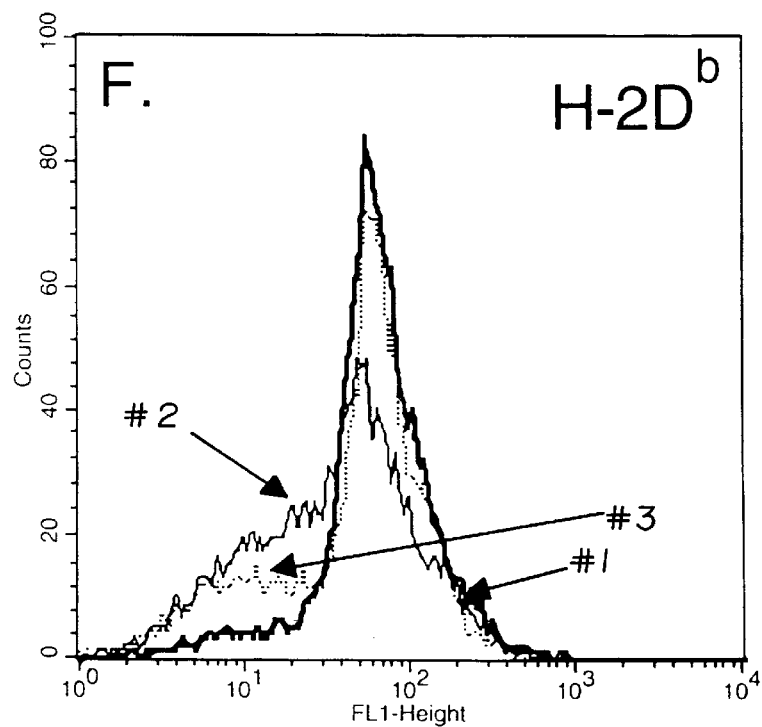

Presentation of DRB1*1502 peptides by the H-2A$^q$ molecule. In light of the previous results. it was hypothesized that presentation of a peptide covering the HV3 region of the DRB1*1502 molecule by H-2A$^q$ might reflect its protective effect on arthritis. To test this hypothesis, B10.RQB3-DRB1*1502 positive and negative animals were immunized with the DRB1*1502 HV3 peptide. For each experiment, two B10.RQB3, B10.RQB3-DRB1*1502 positive or B10.RIII animals were immunized with 200 μg of the DRB1*1502 (DR2Dw12) peptide (65–79) (KDILEQARAAVDTYC) (SEQ ID NO: 3) or 200 μg of the DRB1*1601(DR2Dw21) peptide (65–79) (KDFLEDRRAAVDTYC) (SEQ ID NO: 4). Unlike DRB1*1502 peptide, DRB1*1601 peptide induced only a weak proliferation in all the ice tested. B10.RIII mice showed only a weak response against these peptides, indicating that the binding of DRB1*1502 peptide to H-2A molecules is haplotype-dependent. Lymph node cells were challenged in vitro without peptide (negative control: mean cpm<5,000), with Con A (mean cpm>100,000) or with specific peptides (100 gg/ml). Both groups of animals showed a strong proliferative response when challenged in vitro with the DRB1*1502 peptide (65–79) (FIG. 3). Peptide-specifity was demonstrated when lymph node cells from Bl0.RQB3-DRB1*502 positive and negative littermates failed to proliferate in vitro against HV3 peptide (65–79) of DRB1*1602 (DR2Dw21) which differs from the DRB1*1502 peptide at positions 67, 70, and 71 (FIG. 3). Conversely, B10.RIII mice, carrying the CIA-predisposing haplotype H-2$^r$, showed very little response to both DRB1 peptides. In light of this, it is apparent that the response to DRB1*1502 HV3 peptide is peptide- and haplotype-specific. Thus, B10.RQB3-DRB1*1502 mice are not tolerant to a self DRB1*1502 HV3 peptide.

EXAMPLE 2

Introduction of a Susceptible Human HLA-DO8 Transgene Into class II-Deficient H-2A$^{\beta O}$ Mice

A. MATERIALS AND METHODS

Mice. All mice used in this study were bred and maintained as described in EXAMPLE 1. Derivation of the HLA-DQ8$^+$,H-2A$_\beta^0$ line was achieved as described in FIG. 4. Transgenic B10.M-DQ8 mice were generated by microinjection of HLA-DQA1 and DQB1 genes into fertilized eggs. Specifically, genomic HLA-DQA1*0301 and HLA-DQB1*302 genes were isolated from cosmid clones H11A and X10A, respectively. The cosmid clones Hl1A and X10A were derived from the human B cell line Priess (DR4+, DQ8+, DP3/4+) and are described in Okada et al., Proc. Natl. Acad. Sci. USA 82:3410 (1985). The cosmid clones were provided by J. L. Strominger. Clone H11A contains a 30 kilobase (Kb) DNA insert containing the DQA1*0301 gene, and the DQB1*0302 gene with a truncated promoter, while clone X10A contains a 38 Kb DNA insert containing in its center the DQB1*0302 gene (Okada et al., *Proc. Natl. Acad. Sci. USA* 82: 3410–3414 (1985). For both cosmids, the inserts were released by Sal I restriction enzyme digestion. The resulting constructs, including the coding sequences with associated native regulatory sequences present in the respective cosmid clones, were microinjected separately into (CBA/J x B10.M)F$_2$ and (SJL x SWR)F$_2$ fertilized eggs respectively. General microinjection procedures were substantially as described in Wei et al., In: *Transgenic Mice and Mutants in MHC Research,* Egorov, I. K. & David, C. S. (eds.), Springer-Verlag, pp. 237–246 (1990).

Viable embryos deriving from microinjected eggs were reimplanted into the oviducts of pseudopregnant foster mothers. DQA1-positive and DQB1-positive founders were identified and mated to B10.M mice. Resulting offspring were crossed and back-crossed to produce the transgenic B10.M-DQ8 mice (HLA-DQA1*0301/HLA-DQB1*0302) used for further manipulation. Mouse class II deficient H-2A$_\beta^0$ mice (Cosgrove et al., *Cell* 66: 1051–1066 (1991)) were provided by Drs. Diane Mathis and Christopher Benoist. Analogous class II deficient mice may be obtained commercially from GenPharm International, Mountain View, Calif., USA.

Transgene positive founders and subsequent mice were identified by polymerase chain reaction, using standard procedures, with primers 5'-ACTTGTACCAGT(C/T)TTTA (C/T)GGTCCCTC-3' (SEQ ID NO: 6) and 5'-GAGCGGTAGAGTTG(G/T)AGCGTTTAATCA(C/T) GATGTT-3' (SEQ ID NO: 7), and 5'-AGGATTTCGTGT(A/ T)CCAGTTTAAGGGCAT-3' (SEQ ID NO: 8) and 5'-TGCAAGGTCGTGCGGAGCTCCAA-3' (SEQ ID NO: 9) to amplify the second exons of the DQA1 or DQB1 genes, respectively. Transgene positivity of the founders was also determined by Southern blot analysis of tail DNA with DQB1 and DQA1 cDNA probes using standard protocols (Sambrook et al., *Molecular Cloning: A laboratory Manual* (Cold Spring Harbor Lab., Plainview, N.Y. (1989). Segregation of the HLA-DQ8 transgenes was also monitored by flow cytometric analysis of PBL using the HLA-DQ$_\alpha$ specific mAb IVD12 (see below). Segregation of the mutant H-2A$_\beta^0$ gene was evaluated by flow cytometry by monitoring the expression of the H-2A$^f$ and H-2A$^b$ molecules using the mabs 3F-12 (D. McKean, *J. Immunol.* 136: 2953 (1986)) and AF6–120 (see below), respectively. Mice of both sexes were used in this study and were eight to twelve weeks of age at the start of the experiment.

Flow cytometry. Analysis of HLA-DQ8, murine class I, class II and CD4 expression in PBL was achieved as follows. Mice were bled via the tail artery and the white cell fraction isolated by centrifugation over a ficoll-hypaque gradient. After extensive washing in phosphate buffered saline containing 1% bovine serum albumin and 0.1% sodium azide (PBS/BSA) the cells were incubated with one of the following monoclonal antibodies: IVD12, anti-HLA-DQ$_\alpha$ (Giles et al., *J. Exp. Med.* 157: 1461–1470 (1983)); AF6–120, anti-H-2A$^b$ (Loken et al., *J. Immunol. Meth.* 50: R85–112 (1982)); 7–16.7, anti-H-2A$_\alpha^b$ (kindly provided by Dr. David Mckean); Y17, anti-H-2E$_\beta^b$ (Lerner et al., *J. Exp. Med.* 152: 1085–1101 (1980)); 28-14-8S, anti-H-2D$^b$ (Ozato et al., *J. Immunol.* 125: 2473–2477 (1980)) or phycoerytherin-conjugated anti-mouse CD4 (GIBCO BRL, Gaithersburg, Md.). Following a 30 minute incubation, the cells were washed in PBS/BSA, then, with the exception of the CD4 mAb treated samples, incubated with an FITC-conjugated goat Fab'$_2$ fragment specific for mouse IgG (Accurate Chemical & Science Corp. Westbury, N.Y.). The cells were subsequently washed and fixed with 1% formalin before analysis.

To determine the level of V$_\beta$ TCR expression, mice were sacrificed and the peripheral lymph nodes were removed and homogenized to dislodge the cells. The lymph node cells were then extensively washed with PBS/BSA and approximately $10^6$ cells were incubated with one of the following V$_\beta$ TCR specific mAbs: KT4, rat anti-V$_\beta^4$ (Tomonari et al., *Immunogen.* 31: 333–341 (1990)); MR9–8, mouse anti-V$_\beta$5.1 (Kanagawa et al., *J. Immunol.* 147: 1307–1315 (1991); F23.1, mouse anti-VB8.1.2.3 (Staerz et al., *J. Immunol.* 134: 3994–4002 (1985); F23.2, mouse anti-V$_\beta$8.2 (Kappler et al., *Nature* 322: 35–39 (1988)) and 14-2, rat anti-V$_\beta$14 (Liao et al., *J. Exp. Med.* 170: 135–146 (1989)). Following a 30 minute incubation, the cells were washed, then incubated with FITC conjugated Fab'$_2$ fragments specific for either mouse or rat IgG or rat IgM (Accurate Chemical). After 30 minutes, the cells were washed, then incubated with a 1:1 mixture of phycoerytherin- and RED 613-conjugated mAb specific for mouse CD4 and CD8 respectively (GIBCO BRL). Finally, the samples were washed and fixed with 1 formalin. Both single and three color fluorescent analyses were performed using a FACS Vantage flow cytometer (Becton Dickinson & Co., Mountain View, Calif.).

Induction of CIA. Highly purified native bovine and mouse CII was isolated as described elsewhere (Wooley et al., *J. Exp. Med.* 154: 688–700, (1981)). Lyophilized bovine CII was dissolved overnight at 4° C. in 0.01N acetic acid, then emulsified at a 1:1 ratio with CFA (*Mycobacterium tuberculosis* strain H37 Ra; Difco Laboratories, Inc., Detroit, Mich.). The animals were subsequently immunized with 100 μl (100 μg bovine CII) of the emulsion at the base of the tail. Twenty-eight days later, the animals received a booster injection of 100 Ag bovine CII emulsified in Incomplete Freund's Adjuvant (IFA). The mice were carefully monitored three to four times a week for the onset and progression of CIA from the beginning of the experiment until its termination at twelve weeks postimmunization. The severity of arthritis was evaluated as described in EXAMPLE 1.

Anti-type II collagen ELISA. The level of IgG antibody reactive against bovine and mouse CII was determined using a highly sensitive ELISA technique (Griffiths et al., *J. Immunol.* 153: 2758–2768 (1984)). Briefly, day 35 sera from bovine CII immunized mice were diluted in PBS containing 0.05% Tween 20 and 0.2M NaCl (PNT). Microtiter wells were coated with either bovine or mouse CII dissolved in KPO4 buffer pH 7.6 at 300 μl/well (20 μg/ml of CII) overnight at 4° C. After washing with PNT, the wells were blocked with 1k BSA in PNT. Duplicate serial four-fold dilutions of sera (1:100 to 1:6400) were then added to the wells and incubated at 4° C. overnight. The wells were washed, incubated with a peroxidase conjugated goat anti-mouse IgG (Organon Teknika Corp., West Chester, Pa.) and the color developed using O-phenylenediamine. The amount of total IgG anti-CII antibody was calculated by comparing optical density values with a high titer standard serum arbitrarily determined to contain 100 CII antibody units per/ml of sera.

Histologic evaluation. Mice were sacrificed at the end of the experiment and histological sections of the hind limbs were prepared by the Pathology Department of the Mayo Clinic. Limbs were dissected, the joints decalcified three to four days and then embedded in paraffin blocks. Sections of approximately 6 Am thickness were cut for each joint at differing intervals, mounted and stained with hematoxylin and eosin before analysis.

Statistical analysis. Statistical differences in the mean arthritic severity and mean day of CIA onset between groups was determined using the non-parametric Mann-Whitney U test.

B. RESULTS

Expression of the HLA-DQ8 molecule in H-2A$_\beta^0$ mice induces selection of CD4$^+$T Cells. In an effort to understand the role of HLA class II molecules in RA, the RA-associated HLA-DQ8 molecule was introduced into mouse class II deficient H-2A$_\beta^0$ mice. FIG. 4 illustrates the strategy to derive the HLA-DQ8$^+$,H-2A$_\beta^0$ line. Briefly, as described above, B10.M(H-2$^f$) mice bearing trangenes encoding the α and β genes of the HLA-DQ8 molecule (see above) were mated with H-2A$_\beta^0$ mice. The offspring were screened for HLA-DQ8 expression by flow cytometric analysis of PBL using the HLA-DQ$_\alpha$ specific mAb IVD12. The HLA-DQ8-positive (HLA-DQ8$^+$) ,H-2A$_\beta^{f/0}$ progeny were intercrossed and segregation of the H-2A$_\beta^0$ and H-2A$_\beta^f$ gene was monitored via fluorescent analysis using the H-2A$_\beta^b$ specific mAb 3F-12 and the H-2A$^b$ specific mAb AF6–120. The offspring which typed as HLA-DQ8$^+$,H-2A$_\beta^{0/0}$ were selected and intercrossed to develop the HLA-DQ8+,H-2A$_\beta^0$ and HLA-DQ8-negative (HLA-DQ8$^-$) ,H-2A$_\beta^0$ lines.

FIG. 5, panel A shows that transgenic HLA-DQ8$^+$,H-2A$_\beta^0$ mice expressed the HLA-DQ8 molecule on approximately 30–40% of the PBL population. In addition, expression of HLA-DQ8 was sufficient to induce a partial repopulation of the CD4$^+$T cell subset in the periphery (FIG. 5, panel B). The level of CD4$^+$ cells in PBL of HLA-DQ8$^+$,H-2A$_\beta^0$ animals ranged from 5 to 10%. In no instance, however, did the percentage of CD4$^+$ cells approach the level of control B10 mice. Also, no staining for CD4$^+$ PBL was detected in HLA-DQ8$^-$,H-2A$_\beta^0$ littermates. The percentage of CD8$^+$ cells in HLA-DQ8$^+$,H-2A$_\beta^0$ PBL was approximately two- to three-fold higher than B10 animals and the CD4:CD8 ratio was approximately 1:3 (data not shown).

Given the presence of intracytoplasmic H-2A$_\alpha^b$ and H-2E$_\beta^b$ chains in H-2A$_\beta^0$ mice (Cosgrove et al., cited supra, and Grusby et al., *Science* 253: 1417–1420 (1991)), it was possible that the restored expression of CD4$^+$ cells in the HLA-DQ8$^+$,H-2A$_\beta^0$ line was due to the formation of hybrid A$_{\alpha b}$-DQ8$_\beta$ or DQ8$_\alpha$-E$_\beta^b$ molecules. To eliminate this possibility, PBL from HLA-DQ8$^+$,H-2A$_\beta^b$ mice were analyzed for surface expression of the H-2A$_\alpha^b$ and H-2E$_\beta^b$ molecule. Use of the H-2A$_\alpha^b$-specific mAb 7–16.17 did not result in detection of expression of H-2A$_\alpha^b$ in HLA-DQ8$^+$, H-2A$_\beta^0$ animals (FIG. 5, panel C). Surface expression of the H-2E$_\beta^b$ molecule, using the H-2E$_\beta^b$ specific mAb Y17, was similarly undetected. However, the Y17 mAb reacted strongly with PBL from positive control B10.E$_\alpha^b$ transgenic mice, which express the H-2E$_\beta^b$ chain due to the presence of the H-2E$_\beta^k$ molecule (FIG. 5, panel D). Finally, as expected, HLA-DQ8$^+$,H-2A$_\beta^0$ animals did not express the H-2A$_\beta^b$ chain (FIG. 5, panel E) and expression of the MHC class I molecule $D^b$ was present at a level similar to HLA-DQ8$^-$, H-2A$_\beta^0$ and B10 mice (FIG. 5, panel F).

T cell receptor $V_\beta$ expression on CD4$^+$ cells in HLA-DO8$^+$,H-2A$_\beta^0$ mice. The presence of CD4$^+$ cells in the periphery of HLA-DQ8$^+$,H-2A$_\beta^0$ mice suggested that the HLA-DQ8 molecule induced the positive selection of CD4$^+$, T cell receptor (TCR) positive lymphocytes. To address this issue, lymph node cells from HLA-DQ8$^+$,H-2A$_\beta^0$ animals were analyzed for the expression of $V_\beta$ TCR within the CD4$^+$ subset. As shown in Table 2, HLA-DQ8$^+$,H-2A$_\beta^0$ mice did indeed express a variety of $V_\beta$ TCRs in the CD4$^+$ population. As a comparative control, lymph node cells from B10.T(6R) mice, which express the collagen arthritis susceptible H-2A$^q$ molecule (Wooley et al., cited supra), were also analyzed. The data indicated that in HLA-DQ8$^+$,H-2A$_\beta^0$ mice, the percent expression of the $V_\beta$ TCRs analyzed, although unique, did not appear to be skewed towards a particular $V_\beta$ specificity. A slight elevation in the level of cells expressing the $V_\beta 8$ TCR family was observed. However it is known that in the mouse, this family of TCR is normally present at high levels (Haskins et al., *J. Exp. Med.* 160: 452–459 (1984)). Thus, it appeared that transgenic HLA-DQ8$^+$,H-2A$_\beta^0$ mice possessed an essentially normal $V_\beta$ TCR repertoire within the CD4$^+$ T cell subset.

TABLE 2

T Cell Receptor $V_\beta$ Expression in HLA-DQ8$^+$, H-2A$_\beta^0$ Mice[a]

Percent CD4$^+$N$_\beta$ TCT$^+$ Lymph Node Cells (mean ± S.D.)[b]

| Strain | $V_\beta 4$ | $V_\beta 5.1$ | $V_\beta 8.1.2.3$ | $V_\beta 8.2$ | $V_\beta 14$ |
|---|---|---|---|---|---|
| HLA-DQ8$^+$, H-2A$_\beta^0$ | 4.3 ± 0.1 | 4.2 ± 0.1 | 33.3 ± 6.2 | 8.2 ± 0.8 | 8.2 ± 0.6 |
| B10.T(6R) | 3.4 ± 0.2 | 4.2 ± 3.0 | 17.2 ± 3.2 | 11.1 ± 0.4 | 3.8 ± 0.6 |

[a]Lymph node cells from normal HLA-DQ8$^+$, H-2A$_\beta^0$ and B10.T(6R) mice were isolated and analyzed by flow cytometry for $V_\beta$ TCR expression in the CD4$^+$ subset as detailed above.
[b]Data were calculated based upon three animals per group.

Production of type II collagen antibody in HLA-DO8$^+$, H-2A$_\beta^0$ mice. Typically, murine CIA is induced in susceptible strains of mice bearing the H-2$^q$ or H-2$^r$ haplotype following immunization with type II collagen (CII) in CFA (Wooley et al., *J. Exp. Med.* 154: 688–700 (1981) and *J. Immunol.* 135: 2443–2451 (1985)). Both humoral and cellular immune responses against the CII molecule are essential for the development of severe chronic arthritis (Seki et al., *J. Immunol.* 140: 1477–1483 (1988)) and induction of CIA is critically dependent upon the presence of CII-specific CD4$^+$, TCR $\alpha\beta^+$ T cells (Ranges et al., *J. Exp. Med.* 162: 1105–1110 (1985) and Moder et al., *Autoimmunity* 11: 219–224 (1991)).

Figure 6:
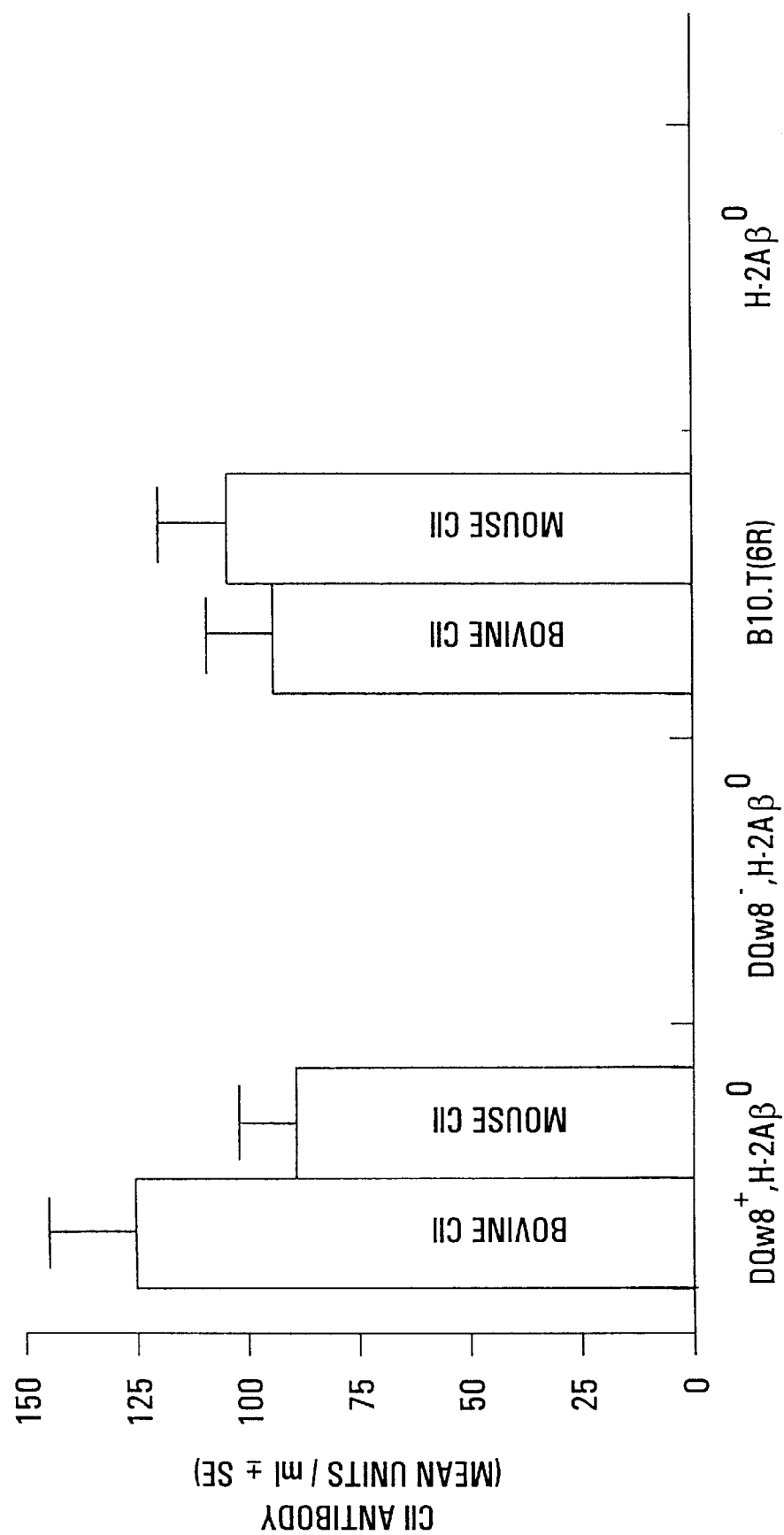
Figure 7A:
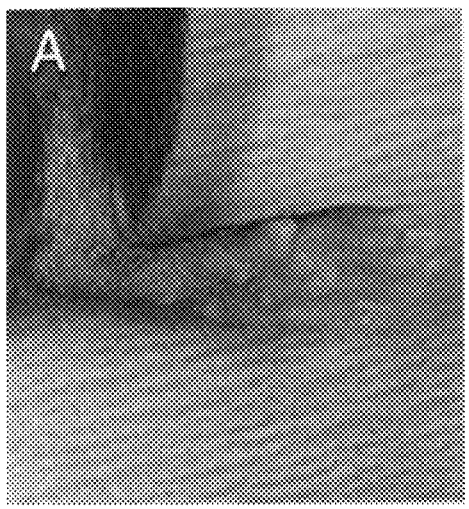
Figure 7B:
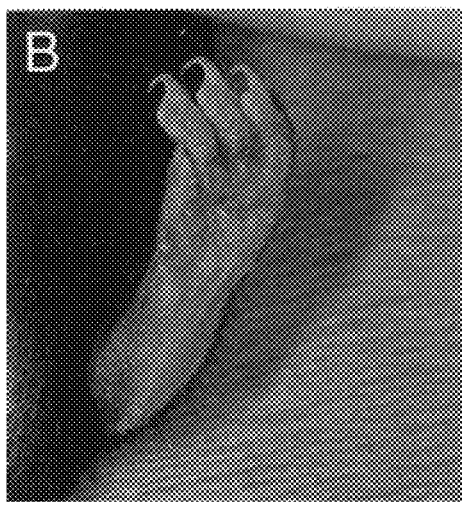
Figure 7C:
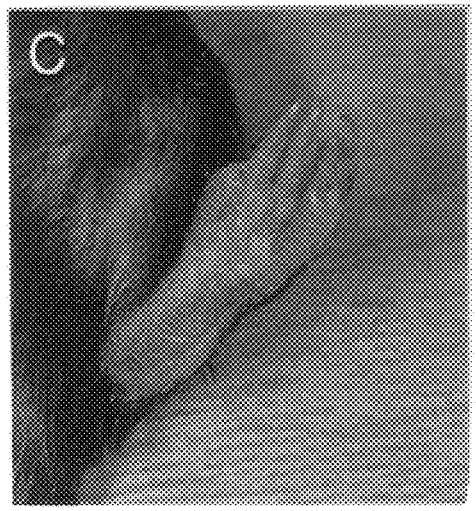
Figure 7D:
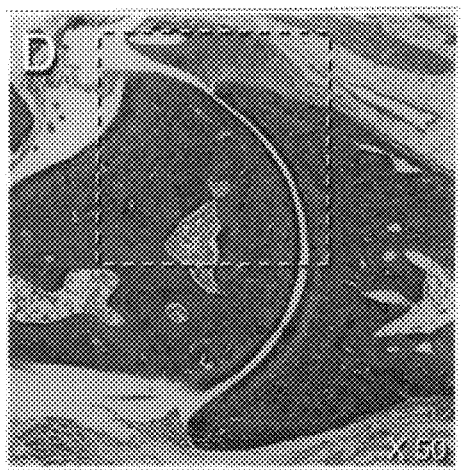
Figure 7E:
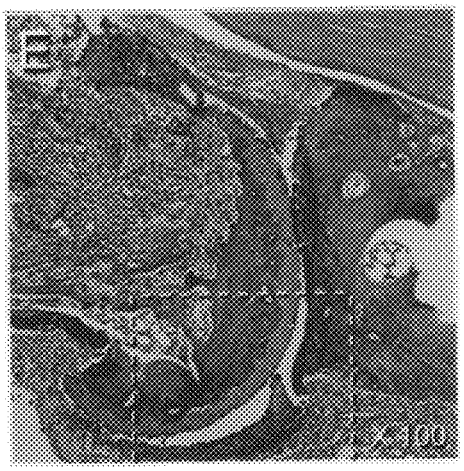
Figure 7F:
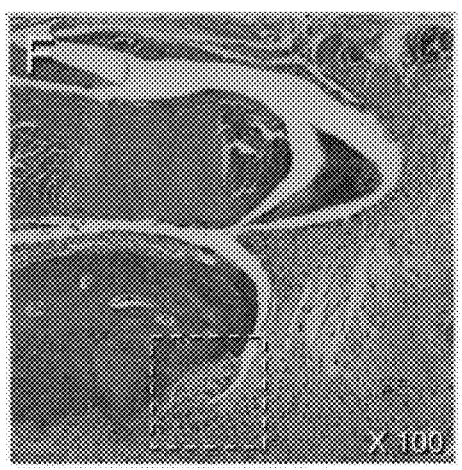
Figure 7G:
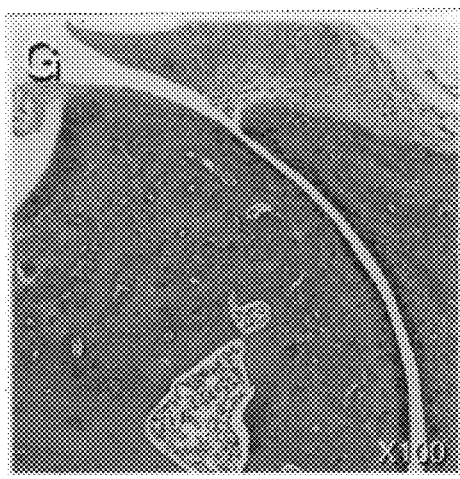
Figure 7H:
Figure 7I:
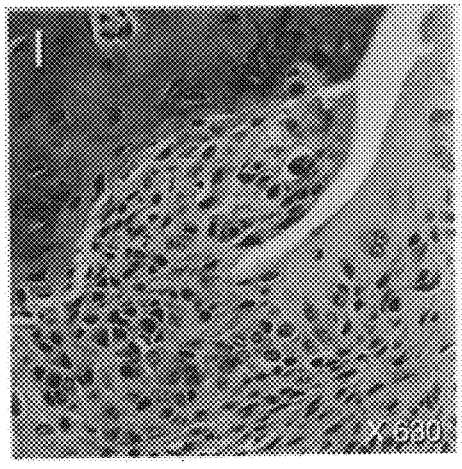

Given the demonstration of CII-reactive cells in the synovial fluid of some RA patients (Ronnelid et al., *Arthritis and Rheum.* 37: 1023–1029 (1994)) together with a putative association of the HLA-DQ8 allele in certain RA populations (Taneja et al., *Rheumatol. Int.* 11: 251–255 (1992)), it was possible that the HLA-DQ8$^+$,H-2A$_\beta^0$ mice possessed the potential to mount a pathogenic immune response against CII. Therefore, HLA-DQ8$^+$,H-2A$_\beta^0$ animals along with transgene negative littermates, positive control B10.T (6R) and negative control H-2A$_\beta^0$ mice were immunized with bovine CII in CFA and monitored for the generation of CII specific antibody (Ab). The mice were immunized on day 0 with 100 μg bovine CII in CFA and boosted with 100 μg bovine CII in IFA on day 28. Sera were collected on day 35 and the level of IgG antibody specific for bovine and mouse CII determined by ELISA. The data were obtained using five to fifteen animals per group. The data revealed that HLA-DQ8$^+$,H-2A$_\beta^0$ mice mounted a strong IgG Ab response against bovine CII (FIG. 6). The level of bovine CII Ab was comparable to arthritis-susceptible B10.T(6R) controls and no CII reactivity was detected in sera from HLA-DQ8$^-$,H-2A$_\beta^0$ littermates or H-2A$_\beta^0$ animals. Moreover, HLA-DQ8$^+$,H-2A$_\beta^0$ sera was highly crossreactive against mouse CII. Like the reactivity against bovine CII, the level of mouse CII reactive Ab was similar to B10.T(6R) sera and the extent of crossreactivity in both strains was greater than 50%. Although many mouse strains of various H-2 haplotypes can mount antibody responses against a heterologous CII species, strong reactivity against homologous mouse CII is limited to strains which bear a CIA-susceptible H-2 haplotype (Holmdahl et al., *Immunogenetics* 24: 84–89 (1986)). Thus, the generation of mouse CII reactive Ab in HLA-DQ8$^+$,H-2A$_\beta^0$ mice suggested that these animals have the potential to develop collagen arthritis.

Development of arthritis in HLA-DO8$^+$.H-2A$_\beta^0$ mice. To determine if the immune response against bovine CII was arthritogenic, bovine CII immunized HLA-DQ8$^+$,H-2A$_\beta^0$ mice, HLA-DQ8$^-$, H-2A$_\beta^0$ littermates, B10.T(6R) animals and H-2A$_\beta^0$ mice were monitored for the onset and development of CIA. As shown in Table 3, experiment 1, HLA-DQ8$^+$,H-2A$_\beta^0$ and B10.T(6R) animals developed severe inflammation, swelling and joint deformity in afflicted limbs (FIG. 7, B and C). Histologic examination of arthritic hind limbs showed that the nature of the inflammatory infiltrate was similar in both strains; a marked synovitis consisting of synovial cell hyperplasia, infiltration of mononuclear cells and erosion of articular cartilage and subchondral bone was observed (FIGS. 7, E, H versus F, I). Transgene negative HLA-DQ8$^-$,H-2A$_\beta^0$ littermates showed no signs of clinical arthritis and histologic evidence of synovial inflammation was not detected (FIGS. 7, A, D and G).

TABLE 3

Susceptibility to Collagen Induced Arthritis in HLA-DQ8$^+$, H-2A$_\beta^0$ Mice[a]

| | | % HLA-DQ8$^+$ | CIA Parameters | | |
|---|---|---|---|---|---|
| | Strain | Cells in PBL (x ± SD) | Clinical Arthritis (Positive/Negative) | Day of Onset (X ± SE) | Arthritis Score[b] (x ± SE) |
| Experiment 1 | HLA-DQ8$^+$, H-2A$_\beta^0$ | 32.2 ± 2.6 | 7/10 | 38 ± 4 | 5.9 ± 1.2 |
| | HLA-DQ8$^-$, H-2A$_\beta^0$ | NA[c] | 0/5 | — | — |
| | H-2A$_\beta^0$ | NA | 0/10 | — | — |
| | B10.T(6R) | NA | 11/15 | 41 ± 4 | 5.4 ± 0.9 |

TABLE 3-continued

Susceptibility to Collagen Induced Arthritis in HLA-DQ8+, H-2A$_\beta^0$ Mice[a]

| | | % HLA-DQ8+ | CIA Parameters | | |
|---|---|---|---|---|---|
| | Strain | Cells in PBL (x ± SD) | Clinical Arthritis (Positive/Negative) | Day of Onset (X ± SE) | Arthritis Score[b] (x ± SE) |
| Experiment 2 | HLA-DQ8+, H-2A$_\beta^0$ | 15.4 ± 4.8 | 5/7 | [d]25 ± 1 | [e]9.0 ± 0.6 |
| | HLA-DQ8−, H-2A$_\beta^0$ | NA | 0/5 | — | — |
| | B10.T(6R) | NA | 8/10 | [d]43 ± 4 | [e]5.6 ± 1.2 |

[a]Mice were immunized with 100 μg bovine CII in CFA on Day 0 and boosted with 100 μg bovine CII in IFA on Day 28. All animals were monitored regularly for the onset and development of CIA until the termination of the experiment at 12 weeks post-immunization.
[b]Mean arthritic score was calculated at the end of the study using arthritic animals only.
[c]Not applicable.
[d]$p < 0.01$
[e]$p < 0.05$ To verify these observations, mice from a second HLA-DQ8+,H-2A$_\beta^0$ line that expresses the HLA-DQ8 molecule on approximately 15% of PBL were immunized with bovine CII and monitored for CIA. Once again, a majority of HLA-DQ8+,H-2A$_\beta^0$ mice developed CIA (Table 3, experiment 2). Interestingly, the onset of clinical arthritis was significantly earlier in the HLA-DQ8+,H-2A$_\beta^0$ line compared to B10.T(6R) mice. Likewise, the severity of CIA was significantly greater in arthritic HLA-DQ8+,H-2A$_\beta^0$ animals. Transgene negative HLA-DQ8+,H-2A$_\beta^0$ littermates did not develop CIA and Ab against bovine CII was not detected (data not shown). Therefore, these findings demonstrated that in class II deficient H-2A$_\beta^0$ mice, expression of the RA-associated human HLA-DQ8 molecule conferred susceptibility to the induction of the RA-like disease CIA.

EXAMPLE 3

Immune Response of HLA-DO8 Transgenic Mice To HLA-DRB1 Peptides

A. MATERIALS AND METHODS

Generation of HLA-D08 (DOB1*0302/DOA1*0301).H-2A$_\beta^0$ transoenic mice. HLA-DQ8+,H-2A$_\beta^0$ mice were generated as described in Example 2, above.

Flow cytometry. Expression of CD4, CD8, HLA-DQ, mouse H-2A and H-2E molecules on peripheral blood lymphocytes (PBLs) was analyzed by flow cytometry using monoclonal antibodies (mAb) GK1.5 (anti-CD4), 53-6-72 (anti-CD8), IVD12 (anti-HLA-DQ), 25-5-16 (anti-H-2Ab), 4D5 and 7-16.17 (anti-H-2A$_\alpha^b$), and Y-17 (anti-H-2E$_\beta^b$) substantially as described in Example 2, above.

Peptide synthesis. The seven DRB1 peptides (65–79) of sequence Lys-Asp-X-Leu-Glu-X-X-Arg-Ala-X-Val-Asp-Thr-Tyr-Cys (SEQ ID NO: 10), where amino acids X at positions 67, 70, 71 and 74 are listed in FIG. 8, were synthesized by the Peptide Core Facility at Mayo Foundation using an automated 430A peptide synthesizer (Applied Biosystems) and purified by high-pressure liquid chromatography. Amino acid compositions were confirmed by sequencing using the Edman's method.

T cell proliferation assay. T cell proliferation assays were preformed as described (Krco et al., Transplantation 54: 920–923 (1992)). For each peptide challenge, 100 μg of peptide emulsified in a saline solution and Complete Freund's adjuvant were injected subcutaneously into the tails of HLA-DQ8,H-2AB$_\beta^0$ and transgene negative full siblings. For dose-response experiments, 100, 10, 1 or 0.1 μg/ml (final concentration) of peptide were added to the cells. For inhibition experiments, 20 μl lo (approximately 5 μg of antibody) of culture supernatants of mAb GK1.5, 53-6-72, IVD12, 25-5-16, 4D5, 7-16.17, Y-17 or MB-40 (anti-HLA-A,B,C) were added to the cells challenged in vitro with 100 μg/ml of DwlO HV3 peptide. Results are representative of at least three independent experiments.

B. RESULTS

Rescue of the CD4+ T cell population by HLA-DO molecules in HLA-DO8 H-2A$_\beta^0$ mice. The MHC class II chains H-2Aab and H-2Eβ$^b$ synthesized in the H-2A$_\beta^0$ mice do not pair with each other. This results in a dramatic reduction in the percentage of CD4+ T cells among PBLs (approximately 0.1%) (Cosgrove et al., cited supra). The expression of the DQB1*0302 and DQA1*0301 genes in these animals (31.5±5.6% of PBLs) restored the CD4 expression in PBLs to a substantial level. The percentage of CD4+ T cells in DQB1*0302.H-2A$_\beta^0$ mice at 6 week-old was approximately 11% compared to 29.5% in B10 animals (Table 4). Moreover, the relative percentages of specific V$_\beta$-bearing CD4+ T cells were comparable to normal B10 animals (Table 3). The possibilities of potential inter-isotypic H-2Eβ/DQA1*0301 and H-2Aα/DQB1*0302 dimers were ruled out by showing the absence of staining on flow cytometry using mAbs 4D5 and 7–16.17 (anti-H-2Aα$^b$-specific), and Y-17(anti-H-2Eβ$^b$-specific) (data not shown). Additionally, the DQB1*0302 chain is not expressed in the absence of DQA1*0301 molecule in single-transgenic mice (data not shown). Therefore, in the absence of mouse class II molecules, the HLA-DQ8 molecule can positively select CD4+ T cells.

TABLE 4

Selection of Peripheral CD4+ T Cells in HLA-DQ8+, H-2A$_\beta^0$ Mice[a]

| Strain | % CD4 (x ± SD) | % CD4/CD44 (x ± SD) | % CD4/Vβ LNC (x + SD) | | | | |
|---|---|---|---|---|---|---|---|
| | | | Vβ4 | Vβ5.1.2 | Vβ6 | Vβ8.2 | Vβ14 |
| HLA-DQ8+, H-2A$_\beta^0$ | 11.2 ± 2.1 | 46.8 ± 0.6 | 6.6 ± 1.6 | 6.5 ± 0.5 | 7.2 ± 1.6 | 8.0 ± 0.1 | 7.7 ± 1.6 |
| HLA-DQ8−, H-2A$_\beta^0$ | 3.7 ± 0.3 | 75.0 ± 3.2 | 5.4 ± 2.6 | 9.3 ± 1.7 | 7.1 ± 2.9 | 14.4 ± 0.7 | 6.5 ± 2.4 |
| B10.T(6R) | 29.5 ± 2.1 | 36.6 ± 4.4 | 6.5 ± 0.4 | 5.2 ± 0.6 | 4.4 ± 0.5 | 12.9 ± 0.4 | 5.4 ± 0.9 |

[a]Lymph node cells were removed and analyzed by flow cytometry as described above. The frequency of CD4+/Vβ positive cells was calculated from the gated CD4+ population shown in column 1. The data are presented as the mean percent positive cells ± standard deviation of three animals per group.

Figure 9A:
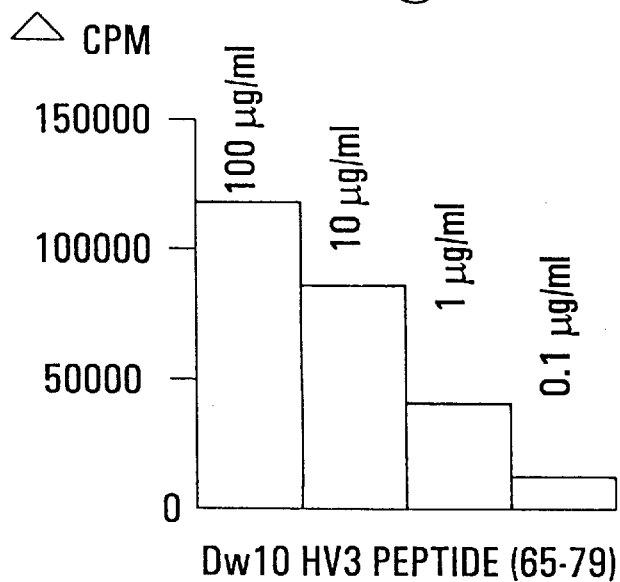
Figure 9B:
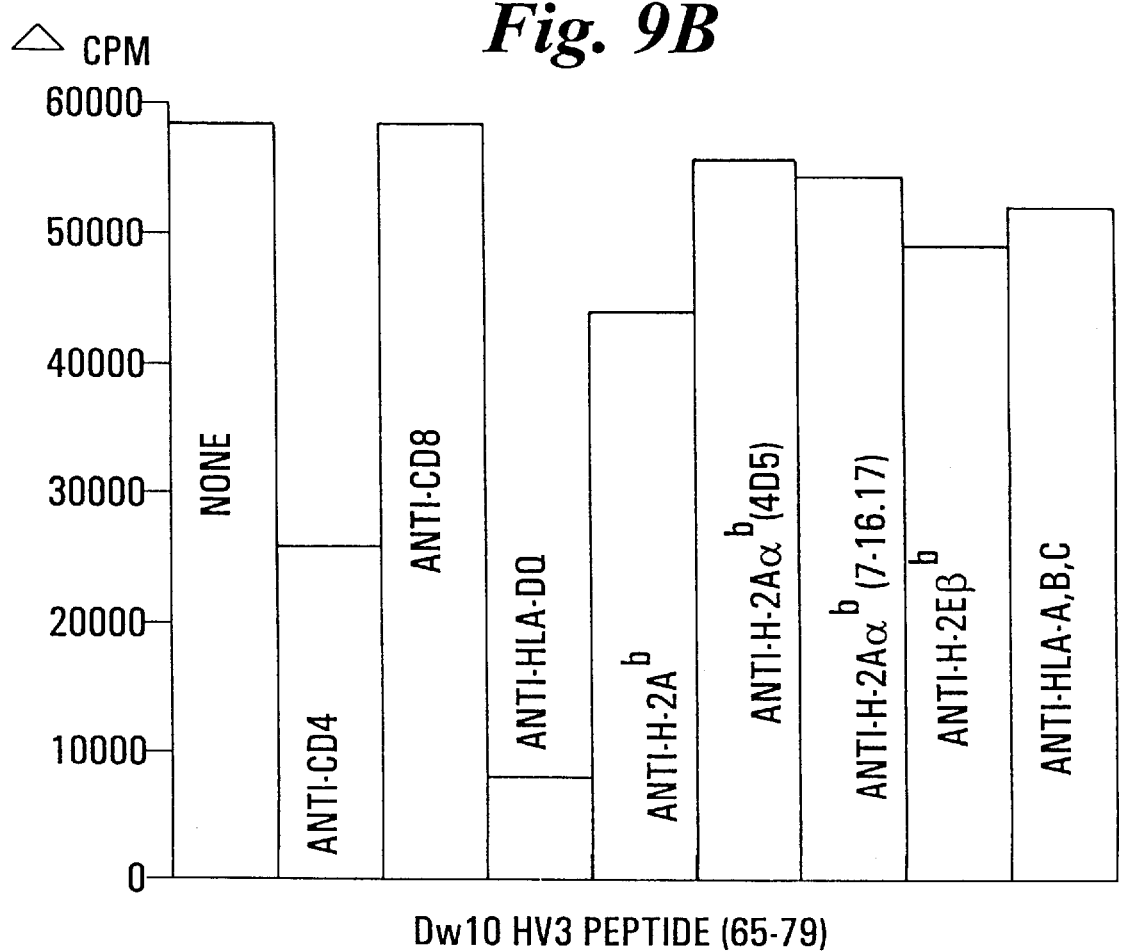

HLA-DO-restricted, CD4+ T cell driven, immune response in HLA-DQ8,H-2A$_\beta^0$ mice. Transgene-positive and negative HLA-DQ8,H-2A$_\beta^0$ littermates were immunized with the Dw10 HV3 peptide (65–79) (FIG. 8). One week later, lymph node cells were isolated and challenged in vitro with varying concentrations of the HV3 peptide (FIG. 9A). A very strong, dose-dependent lymphocyte proliferative response was observed in the HLA-DQ8,H-2A$_\beta^0$ animals, while transgene-negative littermates showed no response (FIG. 9A). When mAb specific for HLA-DQ,H-2A,H-2Aα,H-2Eβ-HLA-A,B,C, mouse CD8 or CD4 molecules were added to the cell suspension, only anti-HLA-DQ and anti-CD4 mAb strongly inhibited the response against Dw1O (65–79) peptide (FIG. 9B). Therefore, the Dw10 peptide-specific T cell proliferation in the HLA-DQ8,H-2A$_\beta^0$ mice is HLA-DQ-restricted and driven by CD4+ T cells.

Immune response of HLA-DO8 H-2A$_\beta^0$ mice to DRB1 HV3 peptides and RA predisposition. The seven DRB1 HV3 peptides covering the region 65–79 and listed in FIG. 8 differ only at positions 67, 70, 71 and 74. They represent all the DR1 and DR4 subtypes, most of the DR2 and DR8 subtypes, and some of the DR5 and DR6 subtypes. The Dw14 peptide possesses an amino acid sequence shared by several DR4 alleles, two out of three DR1 alleles and one of the DR6 alleles; all of them are carried by HLA haplotypes associated with RA predisposition (Nepom et al., *Ann. Rev. Immunol.* 9: 493–525 (1991); Wordsworth et al., *Proc. Natl. Acad. Sci. USA* 86: 10049–53 (1989); Ollier et al., *Rheum. Dis. Clin. North. Am.* 18: 741–59; and Willkens et al., *Arthritis Rheum.* 34: 43–47 (1991) (FIG. 8)). The Dw4 peptide is unique to the RA-associated DRB1*0401 allele, while the Dw13 peptide is shared by several DR4 subtypes that have not been associated with RA, although this latter negative association is less clear (Ollier et al., cited supra). The DwlO peptide corresponds to the HV3 motif of several non-RA-associated alleles including DRB1*0402. Finally, the Dw2, Dw21 and Dw8.1 peptides correspond to motifs found in non-RA-associated DRB1 alleles (Nepom et al., cited supra; Ollier et al., cited supra; Gregerson et al., *Arthritis Rheum.* 30: 1205–13; and Winchester et al., *Rheum. Dis. Clin. North. Am.* 18: 761–783 (1992)).

Figure 10:
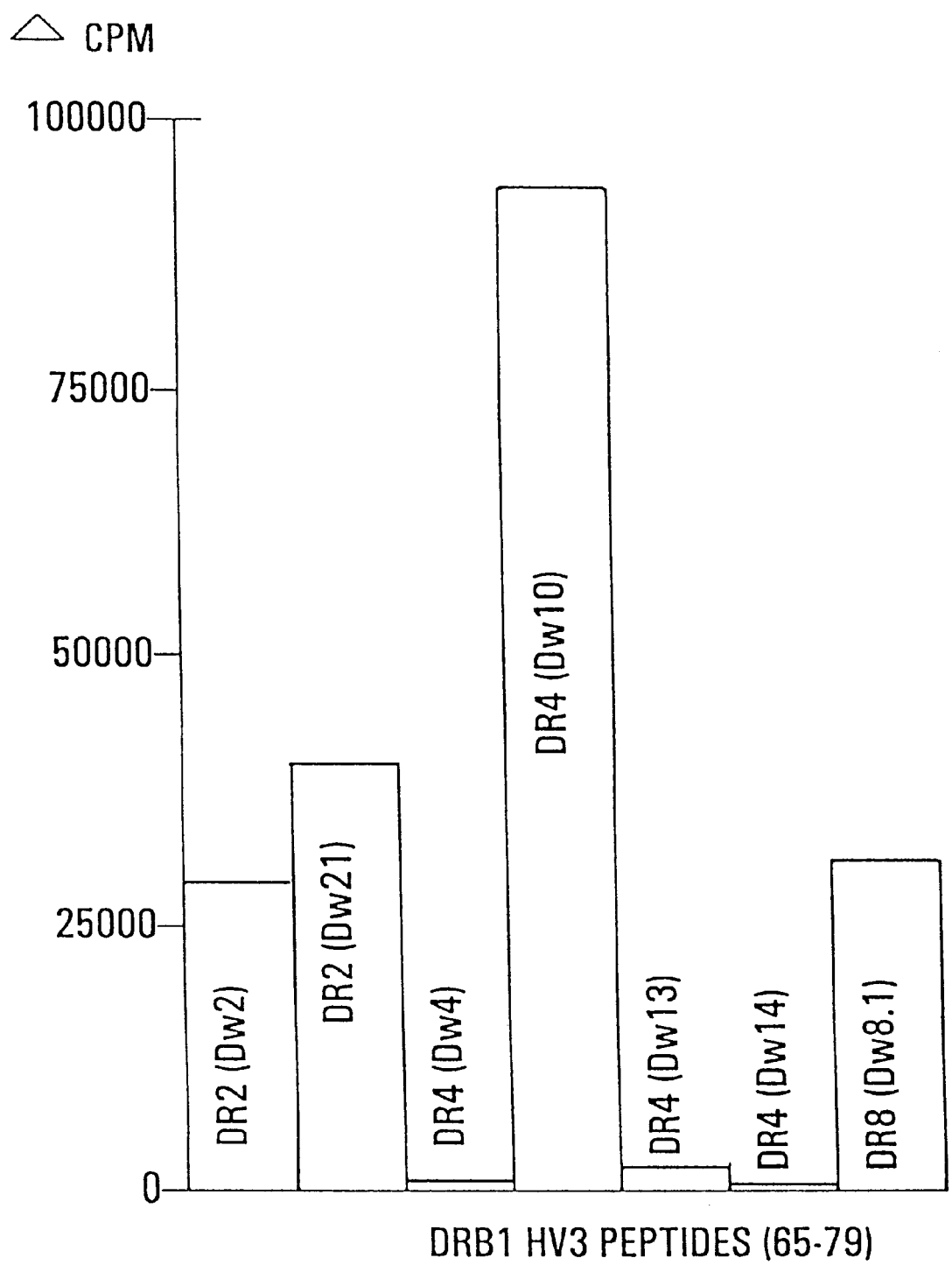

HLA-DQ8,H-2A$_\beta^0$ animals were immunized with the seven DRB1 HV3 peptides (65–79)(FIG. 8). Dw10 induced the strongest proliferative response when lymph node cells were challenged in vitro, followed by Dw2, Dw21 and Dw8.1 HV3 peptides (FIG. 10). Conversely, T cells challenged with Dw4, Dw13 and Dw14 HV3 peptides failed to proliferate (FIG. 10). Therefore, it can be concluded that residues 67, 70, 71 and 74 of the HLA-DRB1 chains effect a HLA-DQ8-restricted proliferative response against DRB1 HV3 peptides (65–79). Specifically, Leu (L) at position 67, found in peptides Dw4, Dw13 and Dwl4, seems to prevent a HLA-DQ8-restricted proliferative response, while Asp (D) at position 70 in peptides Dw10, Dw21 and Dw8.1 seems to promote T cell proliferation (FIGS. 8 and 10). Taken together, these data demonstrate a correlation between the ability of lymph node cells from HLA-DQ8,H-2A$_\beta^0$ mice to proliferate against DRB1 HV3 peptides and the non-association of the corresponding HLA-DR subtypes with RA predisposition.

The foregoing detailed description has been provided for a better understanding of the invention only and no unnecessary limitation should be understood. Other embodiments of the present invention are within the scope of the appended claims.

What is claimed is:

1. A transgenic mouse which lacks functional mouse H-2 class II molecules and is susceptible to collagen-induced arthritis, whose somatic and germ cells contain a transgene comprising human genomic DNA including native transcriptional regulatory elements, wherein said genomic DNA encodes a human HLA-DQ allele associated with susceptibility to rheumatoid arthritis in humans, and wherein said human HLA-DQ allele is expressed on the surface of said transgenic mouse cells.

2. The transgenic mouse of claim 1, wherein said transgene comprises an HLA-DQ8 transgene.

3. A method for identifying peptides potentially effective for prevention or treatment of human rheumatoid arthritis, comprising:

a) providing a transgenic mouse which lacks functional mouse H-2 class II molecules and is susceptible to collagen-induced arthritis, whose somatic and germ cells contain a transgene comprising human genomic DNA including native transcriptional regulatory elements, wherein said genomic DNA encodes a human HLA-DQ allele associated with susceptibility to rheumatoid arthritis in humans, and wherein said human HLA-DQ allele is expressed on the surface of said transgenic mouse cells;

b) administering to said transgenic mouse a test peptide;

c) exposing lymph node cells taken from said transgenic mouse, after said administration, to said test peptide in vitro; and d) identifying said test peptide as potentially effective for prevention or treatment of rheumatoid arthritis if said peptide induces a proliferative response in said lymph node cells.

4. A method for identifying peptides potentially effective for prevention or treatment of human rheumatoid arthritis, comprising:

a) providing a test group of transgenic mice which lacks functional mouse H-2 class I molecules and is susceptible to collagen-induced arthritis, each of said mice whose somatic and germ cells contain a transgene comprising human genomic DNA including native transcriptional regulatory elements, wherein said genomic DNA encodes a human HLA-DQ allele associated with susceptibility to rheumatoid arthritis in humans, and wherein said human HLA-DQ allele is expressed on the surface of said transgenic mouse cells;

b) providing a control group of said transgenic mice;

c) administering collagen to said test group and to said control group;

d) administering to said test group of transgenic mice a test peptide; and e) identifying said test peptide as potentially effective for prevention or treatment of rheumatoid arthritis if said test group mice exhibit reduced susceptibility to collagen-induced arthritis compared to said control group mice.

5. The method of claim 3, wherein said test peptide comprises an HLA-DRB1 peptide.

6. The method of claim 5, wherein said HLA-DRB1 peptide comprises an HLA-DR HV3 peptide.

7. The method of claim 6, wherein said HLA-DR HV3 peptide comprises amino acids 67–74 of the HLA DR protein.

8. The method of claim 4, wherein said collagen administering step is performed prior to administering said test peptide.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

CYTAAGAGGG AGTGTCATTT CTTC                                                    24

(2) INFORMATION FOR SEQ ID NO:2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

TGTGAAGCTC TCMMCAACCC C                                                       21

(2) INFORMATION FOR SEQ ID NO:3:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:3:

Lys Asp Ile Leu Glu Gln Ala Arg Ala Ala Val Asp Thr Tyr Cys
1               5                   10                  15

(2) INFORMATION FOR SEQ ID NO:4:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:4:

Lys Asp Phe Leu Glu Asp Arg Arg Ala Ala Val Asp Thr Tyr Cys
1               5                   10                  15

(2) INFORMATION FOR SEQ ID NO:5:

(i) SEQUENCE CHARACTERISTICS:
        (A) LENGTH: 22 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:5:

Gly Pro Lys Gly Gln Thr Gly Lys Pro Pro Gly Ile Ala Gly Phe Lys
1               5                   10                  15

Gly Glu Gln Gly Pro Lys
            20

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

-continued

```
ACTTGTACCA GTYTTTAYGG TCCCTC                                           26

(2) INFORMATION FOR SEQ ID NO:7:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

GAGCGGTAGA GTTGKAGCGT TTAATCAYGA TGTT                                  34

(2) INFORMATION FOR SEQ ID NO:8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

AGGATTTCGT GTWCCAGTTT AAGGGCAT                                         28

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

TGCAAGGTCG TGCGGAGCTC CAA                                              23

(2) INFORMATION FOR SEQ ID NO:10:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:10:

Lys Asp Xaa Leu Glu Xaa Xaa Arg Ala Xaa Val Asp Thr Tyr Cys
1               5                   10                  15
```